(12) United States Patent
Figini et al.

(10) Patent No.: US 10,813,995 B2
(45) Date of Patent: Oct. 27, 2020

(54) BISPECIFIC ANTIBODY BINDING TRAIL-R2 AND CD3

(71) Applicant: FONDAZIONE IRCCS ISTITUTO NAZIONALE DEI TUMORI, Milan (IT)

(72) Inventors: Mariangela Figini, Milan (IT); Alessandro Satta, Induno Olona (IT); Alessandro Massimo Gianni, Castelveccana (IT); Massimo Di Nicola, Zavattarello (IT)

(73) Assignee: FONDAZIONE IRCCS ISTITUTO NAZIONALE DEI TUMORI, Milan (IT)

( * ) Notice: Subject to any disclaimer, the term of this patent is extended or adjusted under 35 U.S.C. 154(b) by 197 days.

(21) Appl. No.: 15/740,560

(22) PCT Filed: Jul. 1, 2016

(86) PCT No.: PCT/EP2016/065577
§ 371 (c)(1),
(2) Date: Dec. 28, 2017

(87) PCT Pub. No.: WO2017/001681
PCT Pub. Date: Jan. 5, 2017

(65) Prior Publication Data
US 2018/0250396 A1 Sep. 6, 2018

(30) Foreign Application Priority Data

Jul. 1, 2015 (EP) .................................. 15174741

(51) Int. Cl.
*C07K 16/30* (2006.01)
*A61K 39/395* (2006.01)
(Continued)

(52) U.S. Cl.
CPC .... *A61K 39/39558* (2013.01); *C07K 16/2809* (2013.01); *C07K 16/2878* (2013.01);
(Continued)

(58) Field of Classification Search
None
See application file for complete search history.

(56) References Cited

U.S. PATENT DOCUMENTS

| 6,342,369 | B1 * | 1/2002 | Ashkenazi | C07K 14/4747 |
| | | | | 435/252.3 |
| 7,960,515 | B2 * | 6/2011 | Min | C07K 16/2878 |
| | | | | 530/387.1 |
| 2018/0016344 | A1 * | 1/2018 | Moore | C07K 16/2878 |

FOREIGN PATENT DOCUMENTS

WO 2014/161845 A1 10/2014
WO WO-2015184207 A1 * 12/2015

OTHER PUBLICATIONS

Bühler et al., "A Bispecific Diabody Directed Against Prostate-Specific Membrane Antigen and CD3 Induces T-Cell Mediated Lysis of Prostate Cancer Cells," Cancer Immunology, Immunotherapy 57(1):43-52 (2008).

(Continued)

*Primary Examiner* — Claire Kaufman
(74) *Attorney, Agent, or Firm* — Troutman Pepper Hamilton Sanders LLP (Rochester)

(57) ABSTRACT

The present invention concerns the field of cancer immunotherapy, and in particular drugs with low toxicity which can overcome drug-resistance. The present invention concerns novel bispecific antibodies which have the capability of binding both the TRAIL tumor associated antigen and the T lymphocyte CD3. The invention further relates to compositions comprising the bispecific antibodies and a labelling agent, and to pharmaceutical compositions. The present (Continued)

C Single chain Diabody a) TRAIL-R2          b) UCTH-1 (α CD3)

invention also relates to the use of the bispecific antibodies in the treatment of a tumor.

16 Claims, 28 Drawing Sheets

Specification includes a Sequence Listing.

(51) Int. Cl.
  *C07K 16/28* (2006.01)
  *A61P 35/00* (2006.01)
(52) U.S. Cl.
  CPC .......... *A61P 35/00* (2018.01); *C07K 2317/31* (2013.01); *C07K 2317/56* (2013.01); *C07K 2317/626* (2013.01); *C07K 2317/73* (2013.01); *C07K 2317/75* (2013.01); *C07K 2317/92* (2013.01); *C07K 2317/94* (2013.01)

(56) References Cited

OTHER PUBLICATIONS

Cochlovius et al., "Treatment of Human B Cell Lymphoma Xenografts With a CD3 × CD19 Diabody and T Cells," The Journal of Immunology 165:888-895 (2000).
PCT International Search Report and Written Opinion corresponding to PCT/EP2016/065577, dated Oct. 24, 2016.
PCT International Preliminary Report on Patentability corresponding to PCT/EP2016/065577, dated Jun. 23, 2017.

* cited by examiner

A Tandem ScFv 16e2/TR66

B scDb 16e2/UCTH1

C Tandem ScFv 16e2/UCTH1

M15

Jurkat

D scDb Droz/UCTH1

BISPECIFIC ANTIBODY BINDING TRAIL-R2 AND CD3

This application is a national stage application under 35 U.S.C. § 371 of PCT Application No. PCT/EP2016/065577, filed Jul. 1, 2016, which claims the priority benefit of Europe Application No. 15174741.7, filed Jul. 1, 2015.

FIELD OF THE INVENTION

The present invention concerns the field of cancer immunotherapy, and in particular drugs which can overcome drug-resistance.

In particular, the present invention concerns novel bispecific antibodies which have the capability of binding both the TRAIL-R2 and the T lymphocyte CD3.

The invention further relates to pharmaceutical compositions comprising the bispecific antibodies and to the use of the bispecific antibodies in the treatment of a tumor.

STATE OF THE ART

Malignant tumors are one of the greatest causes of death in humans and a very large health problem. In the last decades, scientists have developed many therapies, which, beyond having good results in preclinical studies, have often had poor or null efficacy in subsequent clinical trials, in many cases due to toxicity or to the development of drug-resistance. The discovery of FasL, TNFα and TNF-Related Apoptosis-Inducing Ligand (TRAIL), natural cytokines members of the Tumor Necrosis Factor superfamily, opened new possibilities for the development of new cancer therapeutics thanks to their capability of inducing apoptosis. The first two members of the superfamily, FasL and TNFα, were considered for use as anti-cancer molecules.

After initial excellent results in eradication of tumor cells in vitro, treatments using these two strategies showed the arising of severe adverse effects in vivo, using pre-clinical models: the use of TNFα provoked a strong inflammatory response, while the use of recombinant anti-Fas agonistic antibodies caused severe liver toxicity. TRAIL is a tumor pro-apoptotic ligand for which, contrary to TNFα and FasL, in vivo studies exclude toxicity because it is specific for tumor cells, preserving normal ones. TRAIL-R1 and TRAIL-R2 are both up-regulated in many tumor cells, either naturally or in response to particular chemotherapeutic drugs.

Clinical trials have started with TRAIL receptor agonist compounds, such as recombinant forms of TRAIL and agonistic antibodies. Recombinant TRAIL has the capability of targeting both receptors (TRAIL-R1 and TRAIL-R2) and thus has a greater spectrum of action.

On the contrary, antibodies directed against TRAIL-R1 (mapatumuab) or TRAIL-R2 (drozitumab, conatumumab, lexatumumab and tigatuzumab) can recognize only one receptor and hence they have a minor spectrum of action when compared with recombinant TRAIL, but they have the advantage of not being sequestered by decoy receptors TRAIL-R3 and TRAIL-R4 that have the role of sequestering the ligand preventing TRAIL binding to functional receptors.

While phase I trials, testing these agents, were encouraging (the administration of the recombinant protein on a particular subset of patients was safe and some antitumor activities, with partial or complete responses, have been demonstrated) randomized phase II clinical trials did not reveal anti-cancer activity. In most cases the failure was due to the arising of resistance by tumor cells To by-pass resistance, TRAIL-R2 agonist compounds have been used in association with drugs called "TRAIL sensitizers". Several conventional chemotherapeutic agents (such as doxorubicin, carbo- or cis-platin, irinotecan, bortezomib) are considered to be good "TRAIL-sensitizers" and showed good pre-clinical results, but were disappointing in clinical trials.

After the advent of recombinant technology, there was the upsurge of bispecific antibodies (BsAb) in medical research. These antibodies are able to simultaneously bind two different targets and, for this reason, they could join two mechanisms of action in one molecule or could potentiate an activity. More than 50 different BsAb formats were engineered. BsAbs could be used with a pre-targeting strategy in radio-imaging or radio-immunotherapy or by dual targeting of two different antigens on the same cell or two soluble ligands, but the most frequent use is to retarget immune cells to tumor cells.

In particular good results were obtained with bispecific antibodies that are able to retarget T-cells to lyse tumor cells in a (T-cell receptor) TCR-independent way. Examples of these are Catumaxomab (EpCAM×CD3), made of an IgG produced with hybrid hybridoma technology, and Blinatumomab (CD19×CD3), a Bispecific T-Cell Engager (BiTE). Both molecules have the ability to bind a tumor associated antigen and CD3, the constant portion of the T-cell receptor. In particular, a BsAb of the BITE class, Blinatumomab, was FDA approved in December 2014. BiTEs are made of two linked single-chain antibody fragments (ScFv). The resulting structure is compact and allows the formation of the immunocytolytic synapsis between tumor and immune cells: this structure allows the activation of T-cells with a sub-nanomolar concentration of BiTE and, of note, only when both arms are engaged with their target antigens.

Two bispecific molecules have been developed with the aim of potentiating the cytotoxic armament of T-cells with TRAIL. Each construct consisted of three fusion proteins composed by sTRAIL and a scFv, anti-CD3 or anti-CD7, joined together to form a trimeric form of TRAIL. Despite T-cells armed with these compounds resulting in more cytotoxicity for tumor cells than sTRAIL, the trimeric form of the scFvs anti-CD3 or anti-CD7 could activate T-cells off target causing severe adverse effects like cytokines storm and toxicity on normal cells. The authors, for this reason propose the use of these compounds only to treat tumors restricted to particular anatomically confined regions. The use of a bispecific antibody that contains only one anti-CD3 binding site could by-pass this problem and this BsAb can be used for systemic treatments because the binding of only one CD3 is not sufficient to achieve T-cells activation. Using bispecific antibodies in the Tandem scFv or in single chain diabody format (scDb) formats, T-cells are activated only if there is the formation of immunocytolitic synapse and so only after the binding of the antigen on tumor cells (de Bruyn M. et al, Clinical cancer Res 2011, Sep. 1; 17(17): 5626-37).

Immunotherapy mediated by a bispecific diabody in the field of prostate cancer has been investigated with a bispecific diabody which targets the prostate-specific membrane antigen and CD3 (Buhler P. et al, Cancer Immunol immunother 2008, 57:43-52).

The effect of a diabody on human B cell lymphoma growth was studied by Cochlovius B., et al., Journal of Immunology, 2000, 165: 888-895. A heterodimeric diabody specific for human CD19 on B cells and $CD3_\varepsilon$ chain of the TCR complex was used to investigate efficiency on tumor growth inhibition both in vitro and in vivo on immunodeficient mice bearing B lymphoma xenografts.

WO 2014161845 describes bispecific antibodies targeting the Fibroblast Activation Protein (FAP) and the TRAIL Death Receptor 5 (DR5), which were investigated for use in apoptosis induction.

The need and importance is increasingly felt for the identification of compounds that recognize antigens which are up-regulated in many different tumor cells. TRAIL-R2 may be considered a non conventional tumor associated antigen, in fact on tumors the receptor could be upregulated but could also be present at the same level of normal cells. It has to be noticed that TRAIL-R2 may kill tumor cells preserving normal ones: independently from the level of expression, normal cells developed more mechanisms to resist to the killing induced by TRAIL-R2. Despite this important characteristic, also tumor cells could develop resistance to TRAIL agonistic treatment. It is therefore object of the present invention the development of a BsAb with an anti-TRAIL-R2 arm that specifically kills tumor cells acting as an agonist TRAIL compound, and the anti-CD3 arm that retargets T-cells on tumor cells to lyse them.

SUMMARY OF THE INVENTION

The problem underlying the present invention is that of making available compounds capable of specifically binding and killing tumor cells, in order to permit the manufacture of medicaments for the therapy of related neoplastic pathologies.

This problem is solved by the present finding by the use of bispecific antibodies capable of having these binding specificities and the cytotoxic abilities as described in the present description, examples and attached claims.

The present invention concerns novel bispecific antibodies in the scDb format which have the capability of binding both the TRAIL-R2 and CD3 expressed on T cells.

Besides having the same ability to recognize TRAIL-R2 in a wide range of tumors (such as melanoma, ovarian carcinoma, breast carcinoma, prostate carcinoma, colorectal adenocarcinomas, hepatocellular carcinoma and lung squamous carcinoma) the bispecific antibody here presented can act both as a TRAIL agonist and by triggering lymphocyte cytotoxicity through CD3.

The T-cell activation has been demonstrated to be target specific.

The present invention relates to a single-chain bispecific diabody or fragments thereof comprising:
a. a variable domain of a heavy chain of an immunoglobulin (VH) with a first specificity (A) or fragments thereof, wherein said heavy chain ($VH_A$) variable domain has the amino acid sequence according to SEQ ID NO:1, or direct equivalents thereof, wherein the first specificity (A) is directed against the TRAIL-R2;
b. a variable domain of a light chain of an immunoglobulin (VL) with a second specificity (B), or fragments thereof, wherein said light chain ($VL_B$) variable domain has the amino acid sequence according to SEQ ID NO:3, or direct equivalents thereof, wherein the second specificity (B) is directed against a T lymphocyte CD3;
c. a variable domain of a heavy chain of an immunoglobulin (VH) with the specificity (B), or fragments thereof, wherein said heavy chain ($VH_B$) variable domain has the amino acid sequence according to SEQ ID NO:5, or direct equivalents thereof d. a variable domain of a light chain of an immunoglobulin (VL) with the specificity (A), or fragments thereof, wherein said light chain ($VL_A$) variable domain has the amino acid sequence according to SEQ ID NO:7, or direct equivalents thereof;
wherein the VH and VL domains of the single-chain multiple antigen-binding molecule are connected in the order $VH_A$-$VL_B$-$VH_B$-$VL_A$, wherein each VH and VL domain is connected with a peptide linker, wherein said peptide linker between the $VH_A$ and the $VL_B$ domains and between the $VH_B$ and the $VL_A$ domains consist of four Glycine amino acid residues and one Serine amino acid residue (GGGGS) as encoded by the nucleotide sequence of SEQ ID NO:22, and the peptide linker between the $VL_B$ and the $VH_B$ domains consists of three linker sequences consisting each of four Glycine amino acid residues and one Serine amino acid residues each $(GGGGS)_3$ (as set forth in SEQ ID NO:15).

As will be further described in the detailed description of the invention, the bispecific antibody has the advantage of joining the potential antitumor ability of TRAIL to the ability of bypassing resistance.

In fact, the BsAb has two arms: one arm binds TRAIL-R2 and mimics the pro-apoptotic potential of soluble TRAIL, and the anti CD3 arm which retargets T cells on tumor ones and kills the tumor cells.

In a further aspect of the present invention is a pharmaceutical composition comprising a single-chain bispecific antibody molecule or fragment thereof, according to the present invention and a pharmaceutically acceptable carrier.

According to another aspect, the described invention provides a method for redirecting the cytotoxic action of the T-lymphocytes on a tumor cell, comprising the step of contacting said tumor cell with the single-chain bispecific antibody as disclosed herein.

According to another aspect, the described invention provides a single-chain bispecific antibody or fragment thereof, according to the present invention, for use in the treatment of a tumor.

BRIEF DESCRIPTION OF THE DRAWINGS

The characteristics and advantages of the present invention will be apparent from the detailed description reported below, from the Examples given for illustrative and non-limiting purposes, and from the annexed FIGS. 1-7, wherein:

FIG. 1 shows the cartoon representations of the bispecific construct formats which were engineered to create a bispecific antibody able to bind TRAIL-R2 and to retarget efficiently T-cells on tumor cells, as described in Examples 2 and 3.

FIG. 2A: size exclusion chromatography profile of the tandem scFv BsAb 16e2/TR66 which loses its binding ability after few days and had the tendency to aggregate.

FIG. 2B: size exclusion chromatography profile of the scDb 16e2/hUCTH1 which resulted stable and the aggregates did not exceed 0.5% also after 2 years.

FIG. 2C: size exclusion chromatography profile of the Tandem scFv format, built using as anti-CD3 the hUCTH1. This construct recognizes the CD3 but was not able to recognize TRAIL-R2.

FIG. 2D: size exclusion chromatography profile of the scDb, which was built also using as anti-TRAIL-R2 Drozitumab a derivative of the 16e2 that varies from 16e2 only in few aminoacids and as anti-CD3 the hUCTH1. In this case the construct works only for few days and the yield of production was very low.

The test confirmed the binding specificity of the BsAb: the scDb binding profiles (first row) followed the expression of the receptor on the diverse cell lines. A commercial anti-TRAIL-R2 antibody or TR66 anti-CD3 antibody for Jurkat (second row) have been used as controls.

Empty peak: negative control; grey peak: scDb plus anti-Tag and anti-mouse antibodies (first row) or commercial antibody plus anti-mouse antibody (second row).

FIG. 3B: Biacore analysis (a plasmon surface resonance based method that permits to follow the kinetic interaction between two proteins in real time) left panel: demonstrated that the scDb16e2/hUCTH1 had both a fast attach and a fast detach from TRAIL-R2 recombinant protein immobilized on a CM5 chip. The dissociation constant at the equilibrium (KD) is 148 nmoles/L and was calculated using 5 different concentrations, starting from 400 nM of scDb till 25 nM.

right panel: sensorgram from the BIAcore illustrating competition study. At the black arrow 1 µM of sTRAIL was injected to saturate all the receptors present on the chip; at grey arrow 400 nM of scDb16e2/hUCTH1 was injected. No binding of scDb on saturated receptor was observed revealing that the two compounds are in competition for the same binding site.

FIG. 3C: SDS page and western blot analysis revealed that the mass of the scDb is about 54 kDa.

FIG. 3D: SELDI-TOF analysis which confirms the data obtained in FIG. 3C.

Figure 4:
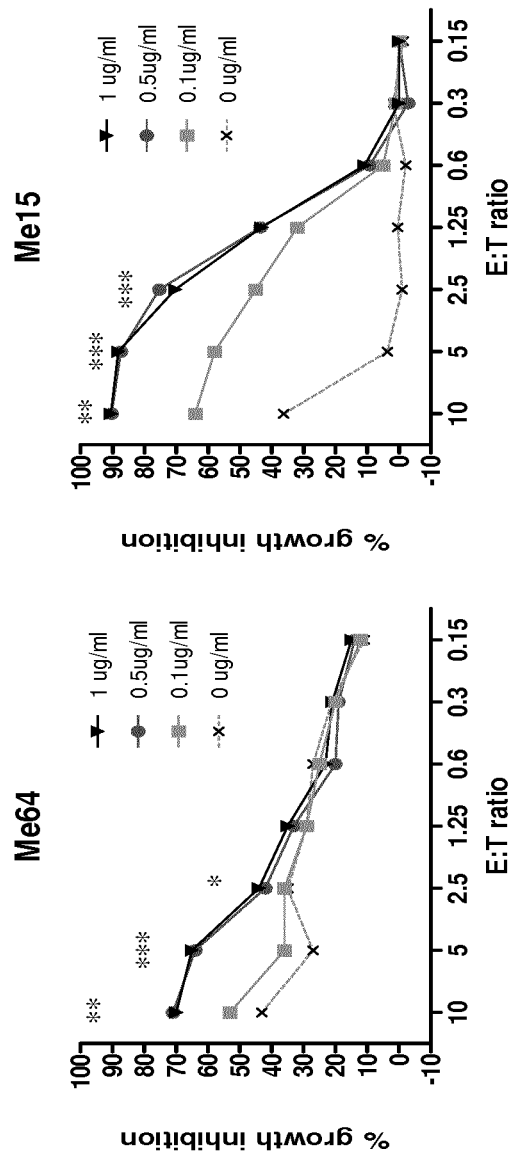
Figure 4:
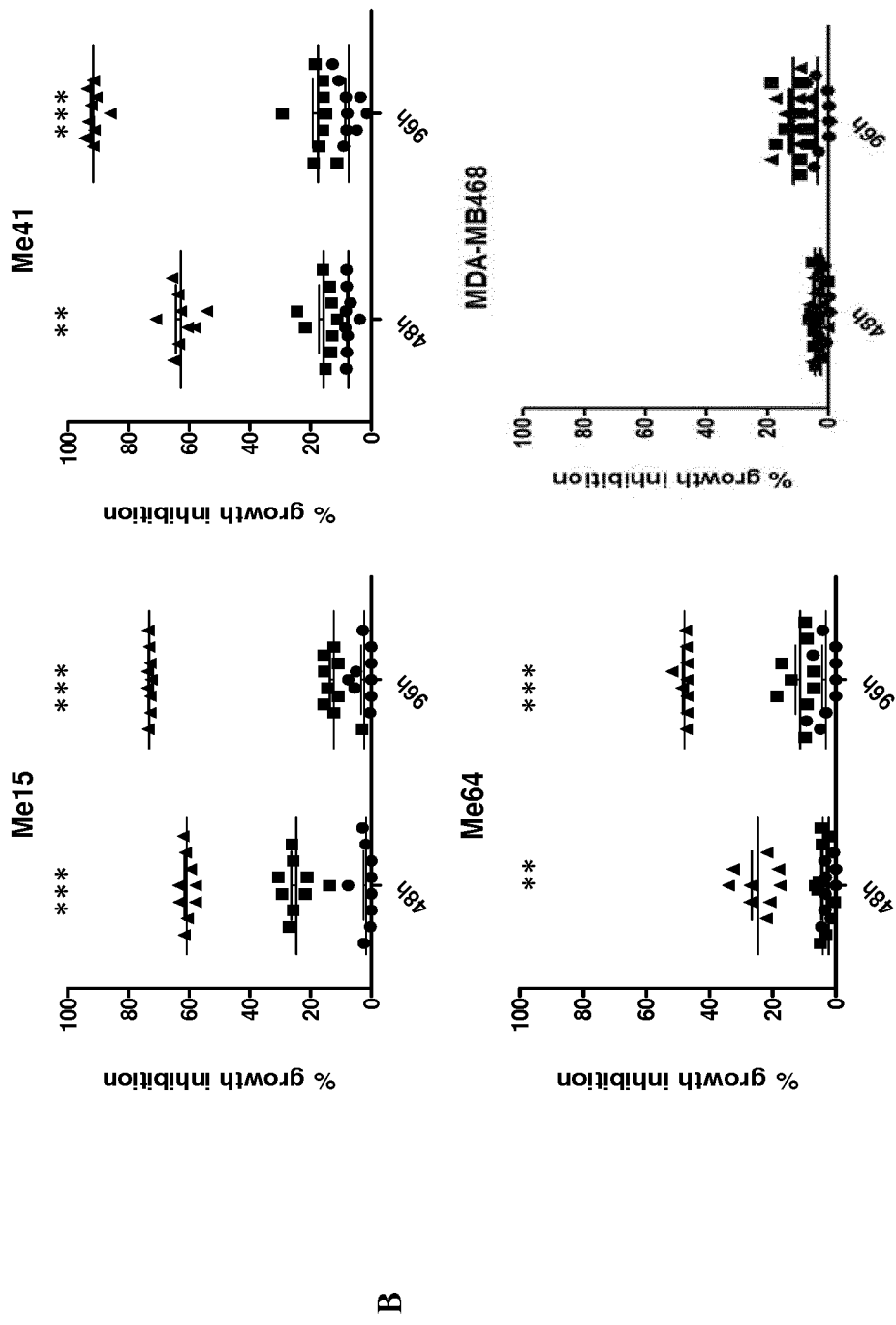

FIG. 4 Cytotoxic Activity FIG. 4A. Cytotoxicity of the bispecific scDb 16e2/hUCTH1 on M64 (low-expression of TRAIL-R2 and sTRAIL resistant) and M15 (high-expression of TRAIL-R2 and sTRAIL sensible) melanoma cell lines. Different E:T ratio and concentration were used to evaluate the scDb cytotoxicity. ScDb was used at 1, 0.5 and 0.1 pg/ml with E:T ratio starting from 10:1 until 0.15:1 with F2 dilutions in cytotoxicity experiments to determine optimum scDb dose and E:T ratio. Experiments indicated that the best E:T ratio was 5:1 and we observed absence of cytotoxicity on non treated tumor cells and that at concentration of 0.5 ug/ml the activity of the scDb reach the plateau, as described in Example 3.

FIG. 4B. Graphs illustrated 9 different growth inhibition assays, performed to test reproducibility of treatment results. A different batch of PBLs (derived from healthy donors) was used in each experiment. The treatment of M64, M41 and M15 with 0.5 ug/ml of scDb plus PBLs (E:T ratio of 5:1) gave similar results in all the experiments. TRAIL-R2 negative MDA-MB-468 did not respond to treatment, as expected.

Figure 4C:
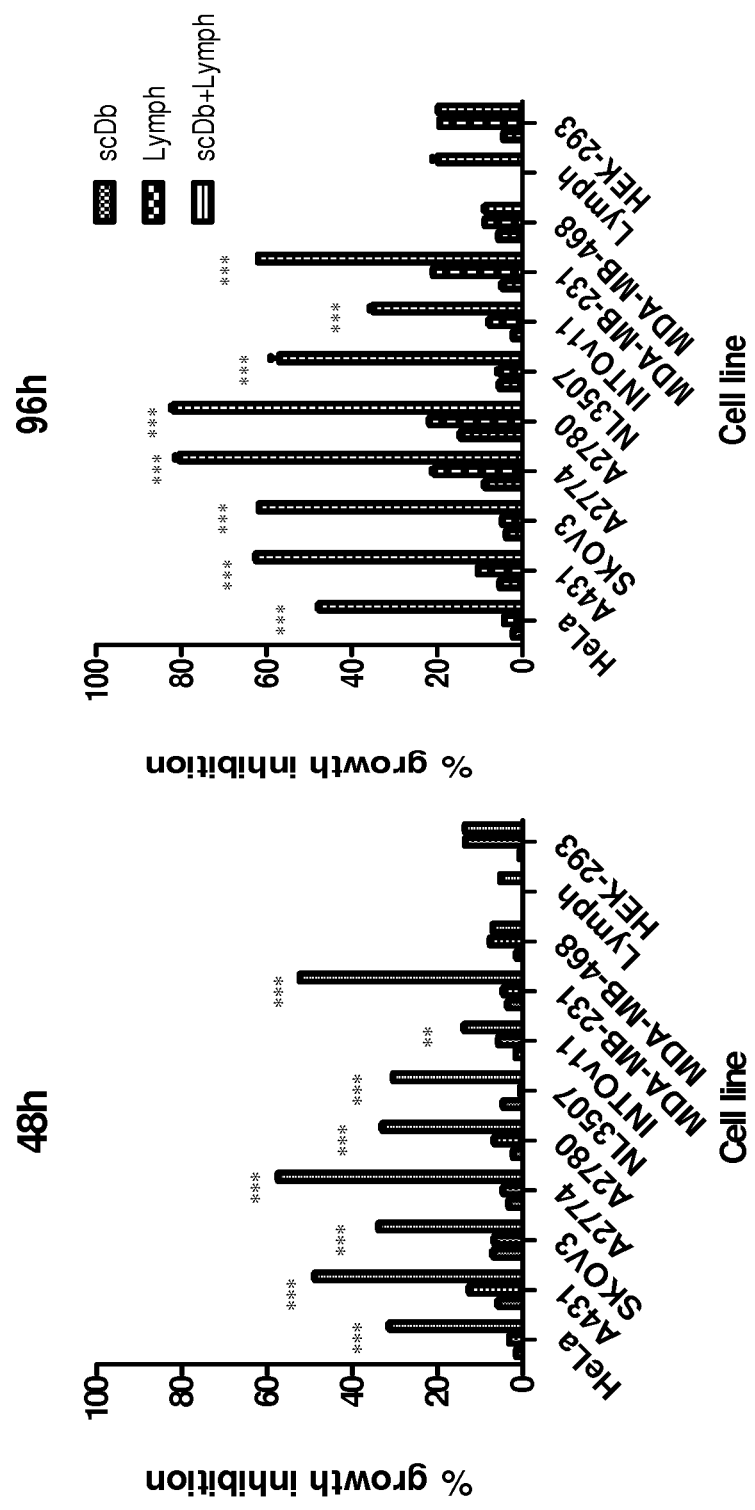

FIG. 4C. Antibody-dependent PBLs-mediated growth inhibition was performed for several cancer cell lines using a concentration of scDb of 0.5 µg/ml and a E:T ratio of 5:1. Cells were exposed to treatment for 48 or 96 hours. The treatment induced proliferation inhibition on all tested tumor TRAIL-R2 positive cell lines; no toxicity was observed on TRAIL-R2 negative MDA-MB-468 cells and on normal TRAIL-R2-high expression HEK293 cells.

Figure 4D:
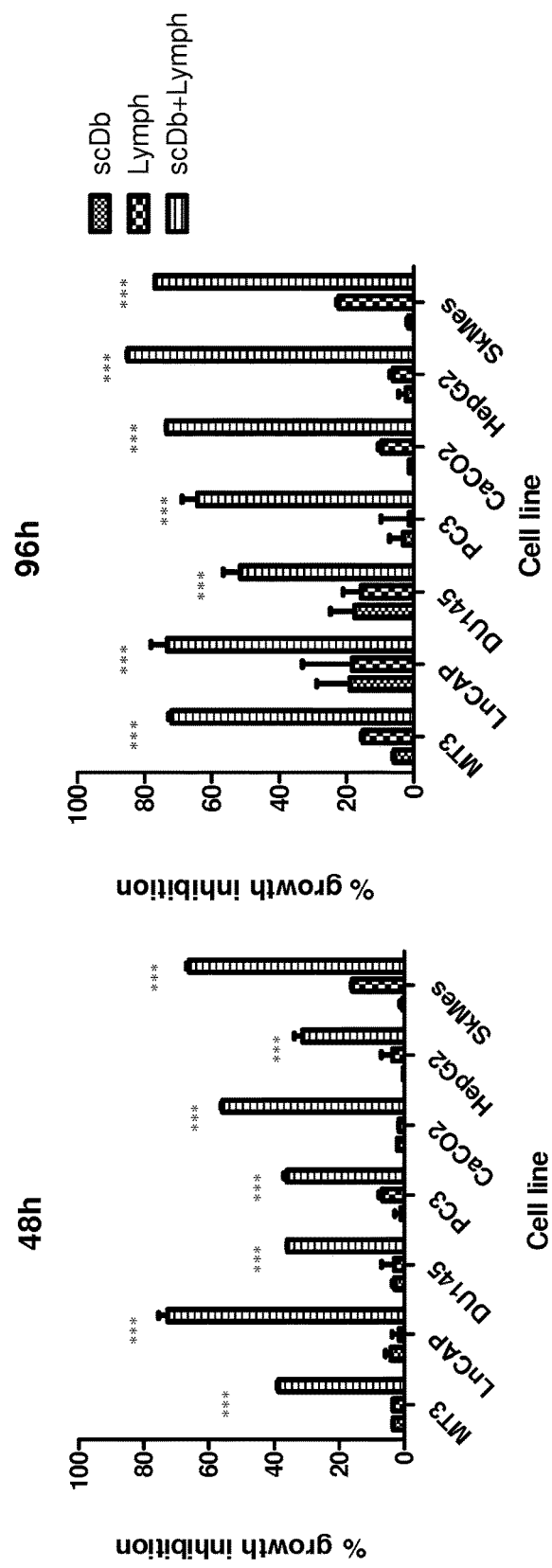
Figure 4:
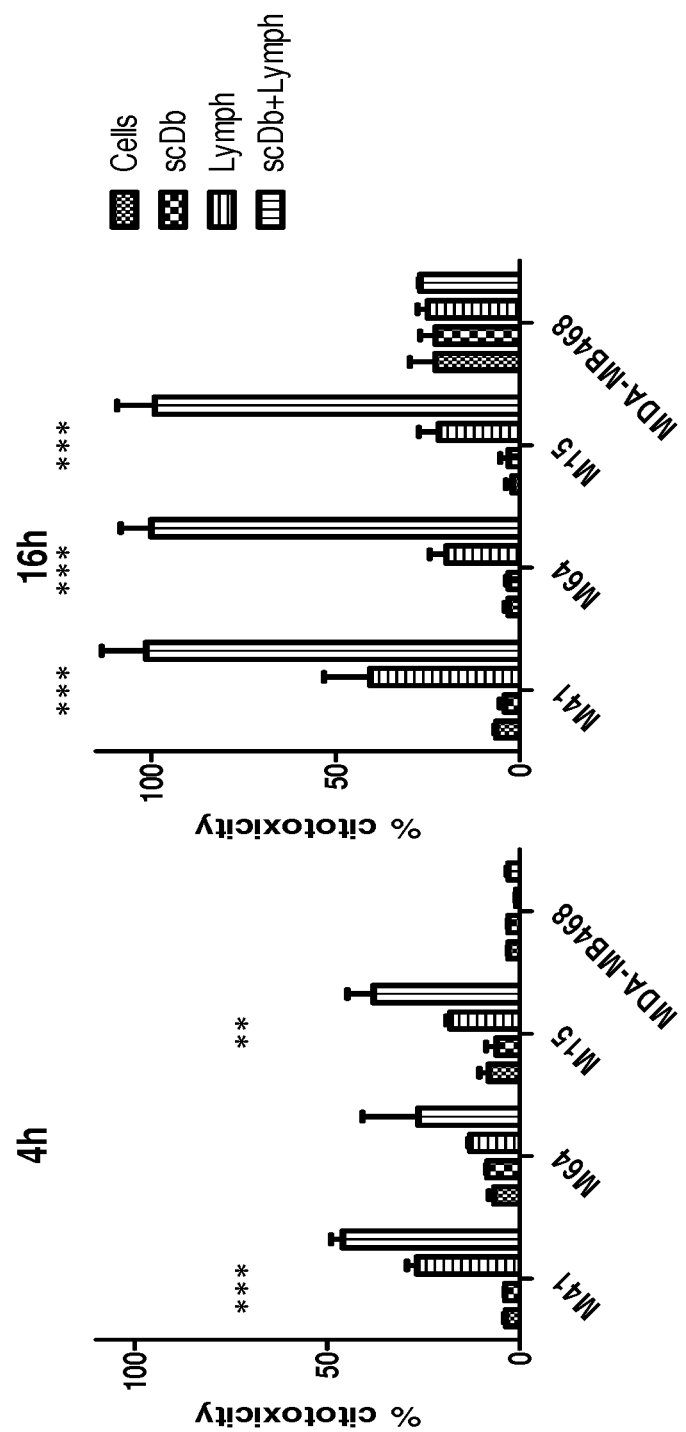

FIG. 4D. Antibody-dependent PBLs-mediated growth inhibition was performed for several cancer cell lines using a concentration of scDb of 0.5 µg/ml and a E:T ratio of 5:1. Cells were exposed to treatment for 48 or 96 hours. The treatment induced proliferation inhibition on all tested tumor TRAIL-R2 positive cell lines.

FIG. 4E. Calcein-AM release assay. Tumor cells were loaded with calcein-AM that, once entered in the cells, was esterified and became fluorescent. Cells were treated for 4 and 16 hours to measure T-cell toxicity, when redirected with scDb. Graphs show the percentage of lysed cells. After 4 hours about 45-50% of TRAIL-R2 high-expression M15 and M41 were lysed, while for low expression M64 the variation of treated cells was not significative in comparison to control. After 16 hours 100% of the treated cells, also M64, were lysed in consequence of treatment. No lysis was observed in TRAIL-R2-MDA-MB-468 cells. Graph represents mean±SD, n=5, p<0.01, *p<0.001.

Figure 5A:
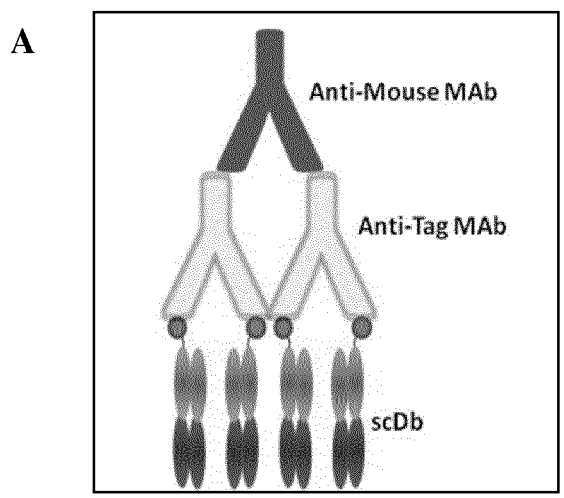
Figure 5B:
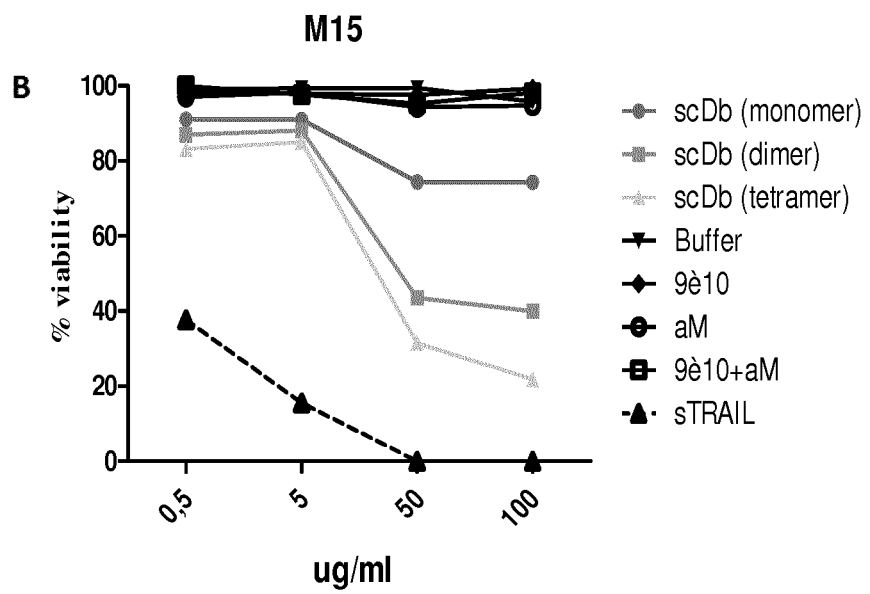
Figure 5C:
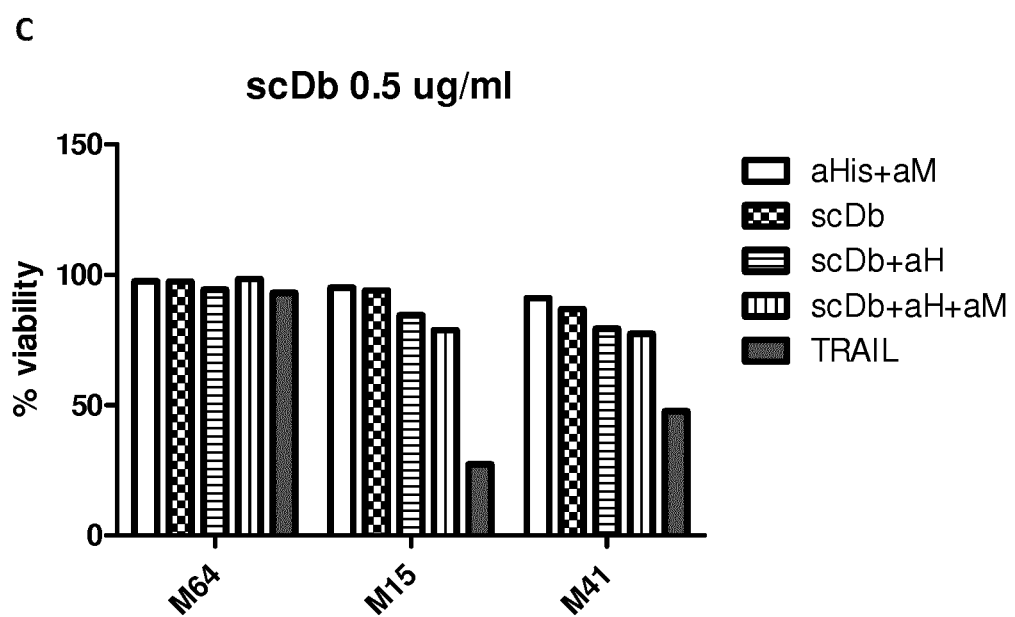
Figure 5:
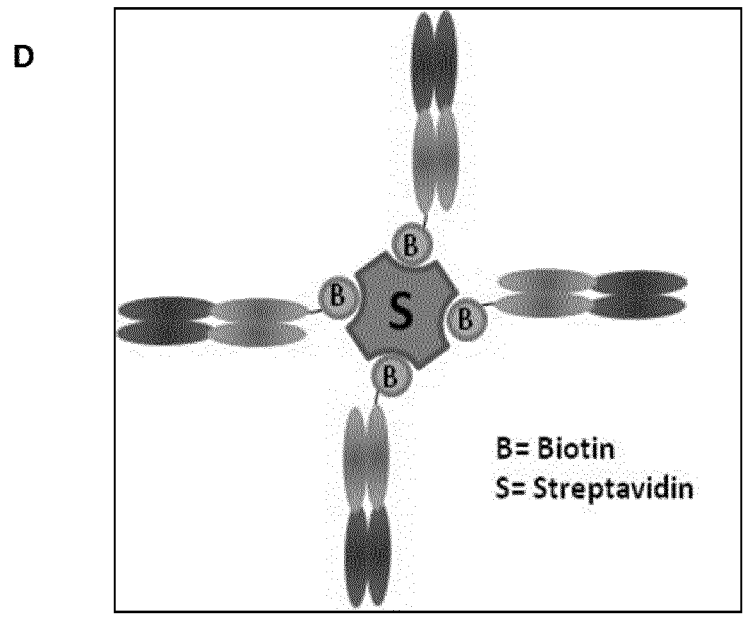

FIG. 5 Agonistic Activity

FIG. 5A Cartoon representing the way by with scDb has been multimerized: anti-tag MAb could bind tag present on scDbs dimerizing them. Adding anti-mouse MAb the anti-tag/scDb conjugate could dimerize and induce tetramerization of BsAbs.

FIG. 5B Agonistic proapoptotic activity of scDb against sTRAIL sensitive M15 cells. M15 cells were treated with several doses of scDb alone or equal doses of scDb dimerized or tetramerized according to description in FIG. 5A. Cell toxicity was assessed after 24 hour of treatment using CellTiterGlo assay. sTRAIL, at equal scDb concentration, was used like positive control. Results were expressed as percentage of negative control.

FIG. 5C Agonistic proapoptotic activity of scDb on melanoma cells with different sensitivity to TRAIL. sTRAIL sensitive M15, semi-resistant M41 and resistant M64 were treated, with 0.5 µg/ml of scDb alone or multimerized with anti-tag and anti-mouse strategy, for 24 hours (C). Soluble TRAIL (100 ng/ml) was used like positive control of receptor-mediated apoptosis induction.

FIG. 5D Cartoon representing tetramerization of scDb by Biotin-straptavidin binding. ScDb was biotinilated in vitro using Biotin N-hydroxy-succinimide ester (Sigma) and incubated with straptavidin. Tetrameric scDb was purified by size exclusion chromatography.

Figure 5E:
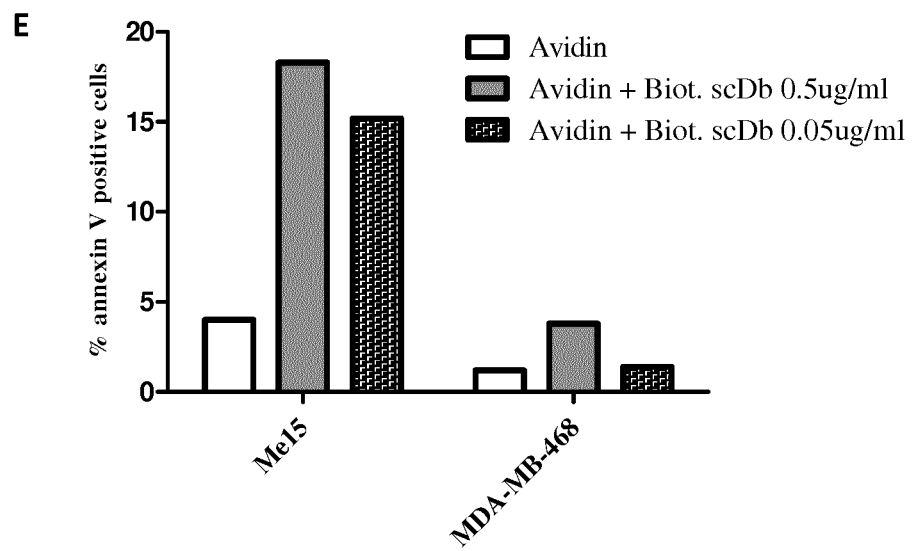

FIG. 5E Agonistic proapoptotic activity of streptavidin tetramerized scDb against sTRAIL sensitive M15 cells. M15 cells were treated with 0.5 or 0.05 µg/ml of tetramerized scDb. Cell toxicity was assessed after 24 hour of treatment using CellTiterGlo assay. Results were expressed as percentage of negative control.

FIG. 6 ScDb-mediated T-cell activation analysis.

Figure 6A:
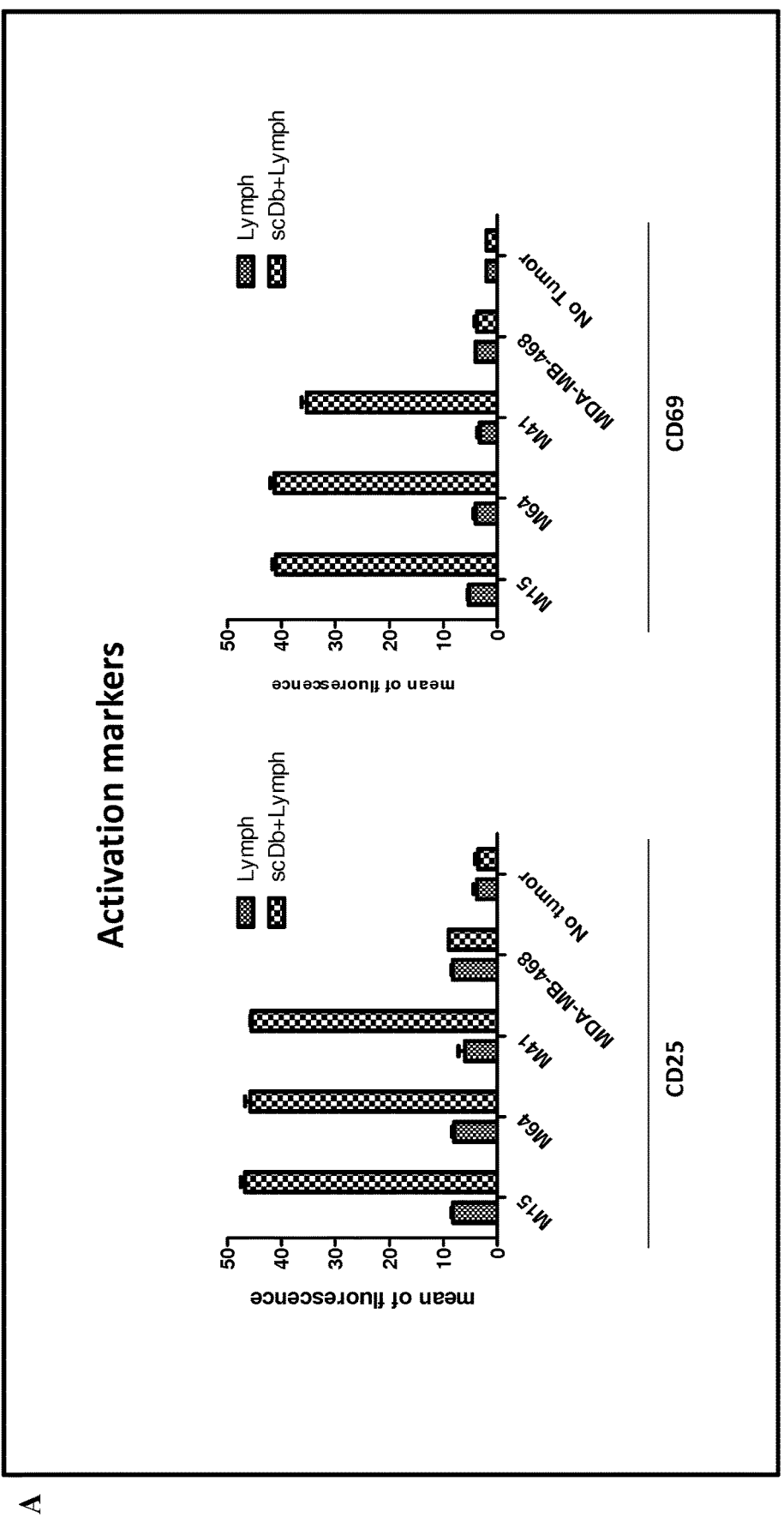

FIG. 6A Freshly isolated T-cells were incubated, in concentration E:T=5:1, with or without 0.5 µg/ml of scDb on 3 different melanoma tumor cells lines, as described in Example 3.

Expression of CD25 and CD69.

Cell surface expression of CD69 and CD25, activation-associated markers on redirected T-cells, was measured by flow cytometry analysis 24 h after starting the co-culture. Graphs represent the percentage of positive cells in comparison to total T-cell population for each marker. T-cells self-activation was measured incubating T-cells without tumor cells. The results represents the mean±SD of 3 different assays performed with 3 diverse batch of healthy donor derived T-cells.

Figure 6B:
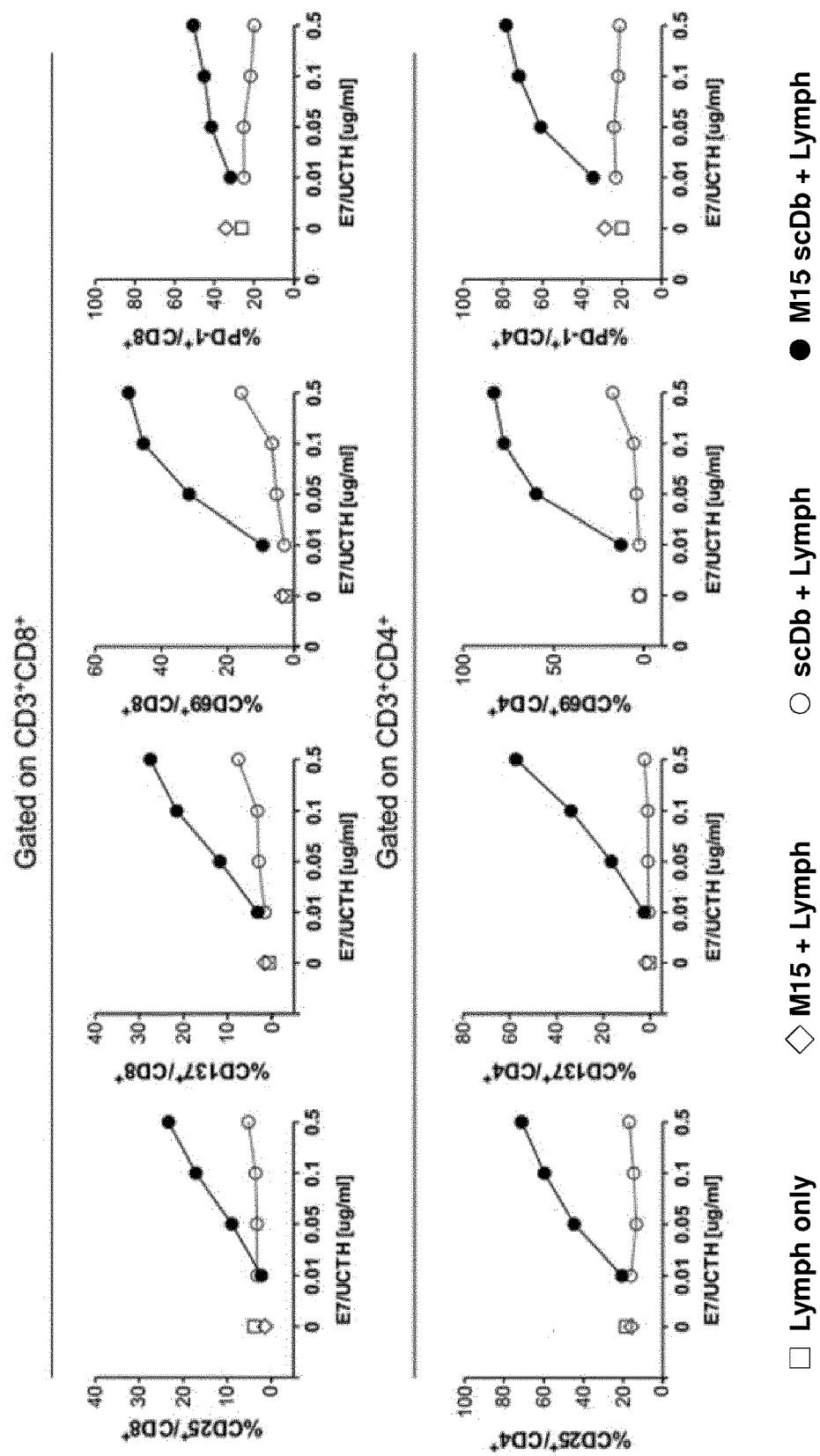

FIG. 6B Freshly isolated T-cells were incubated, in concentration E:T=5:1, with or without a concentration in titration from 0.01 to 0.5 µg/ml of scDb on M15 tumor cells lines, as described in Example 3.

Expression of CD25, CD137, PD-1 and CD69 on CD4 and CD8 redirected T-cells.

Cell surface expression of CD137, PD-1, CD69 and CD25, activation-associated markers on redirected T-cells, was measured by flow cytometry analysis 16 h after starting the co-culture. Graphs represent the percentage of positive cells in comparison to total CD4+ or CD8+ T-cell population for each marker. T-cells self-activation was measured incubating T-cells without tumor cells.

Figure 7A:
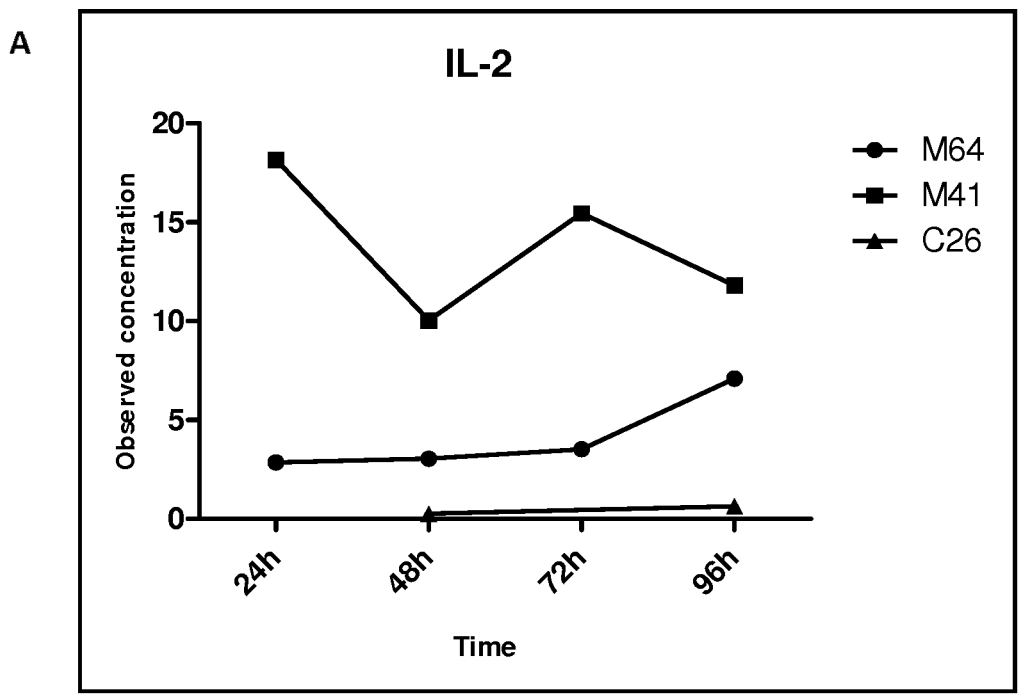
Figure 7B:
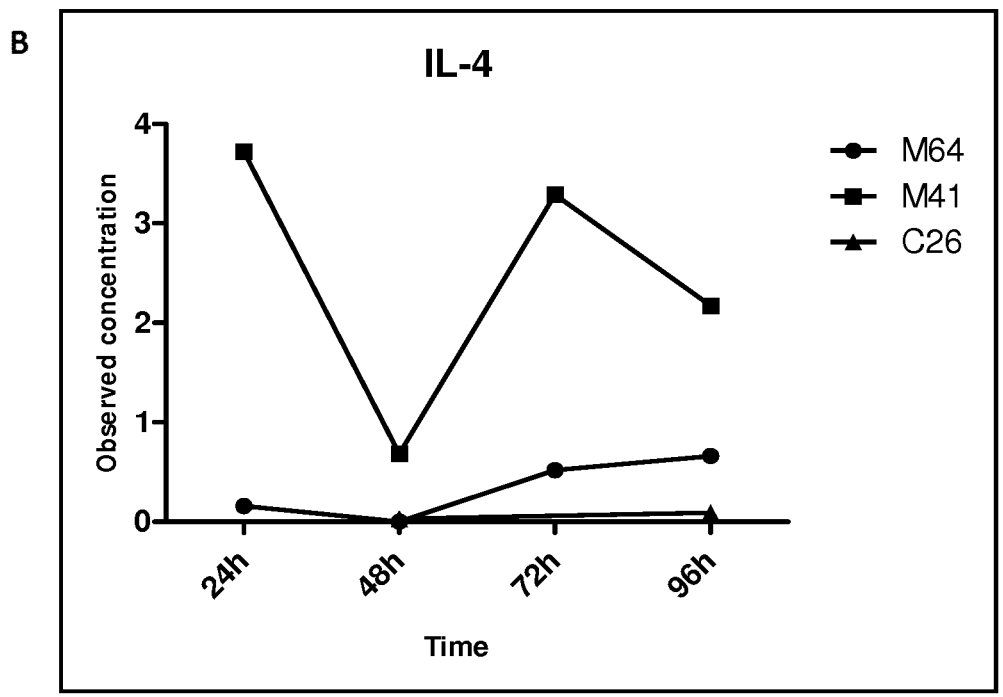
Figure 7C:
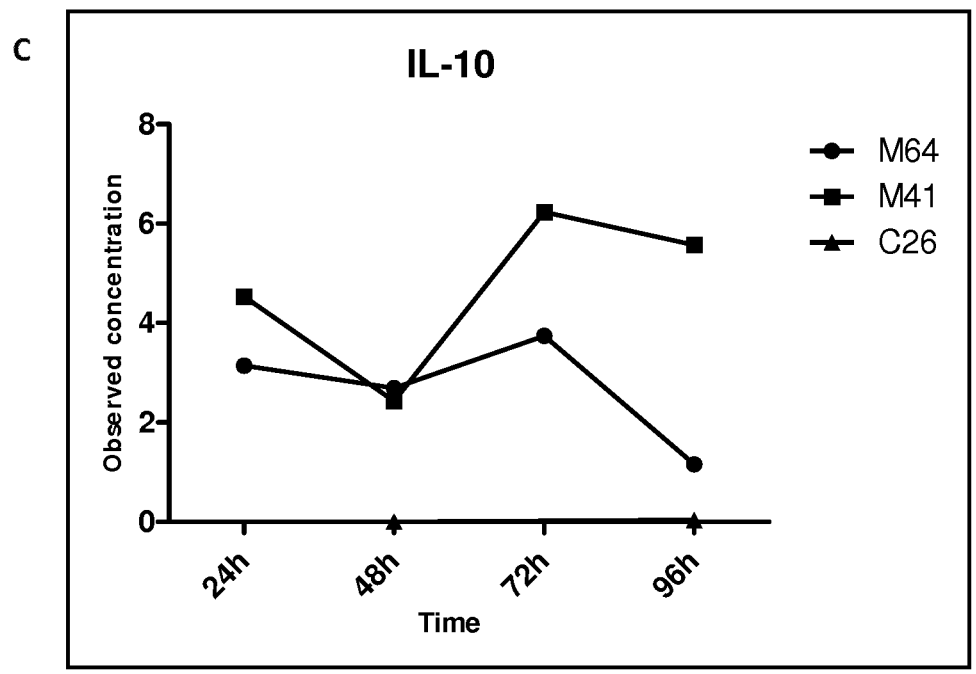
Figure 7D:
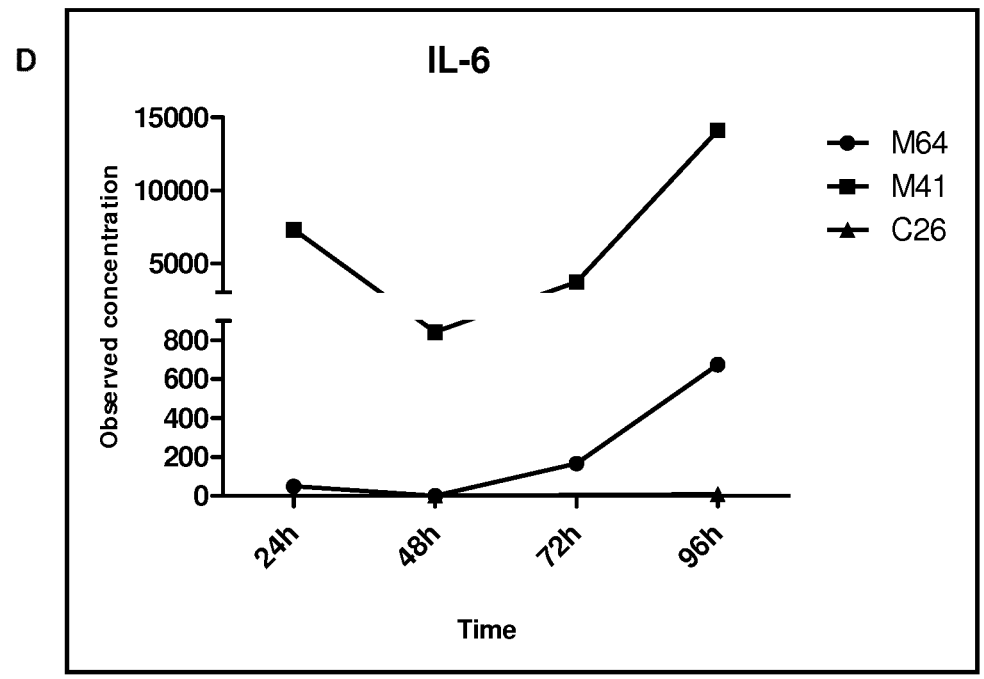
Figure 7:
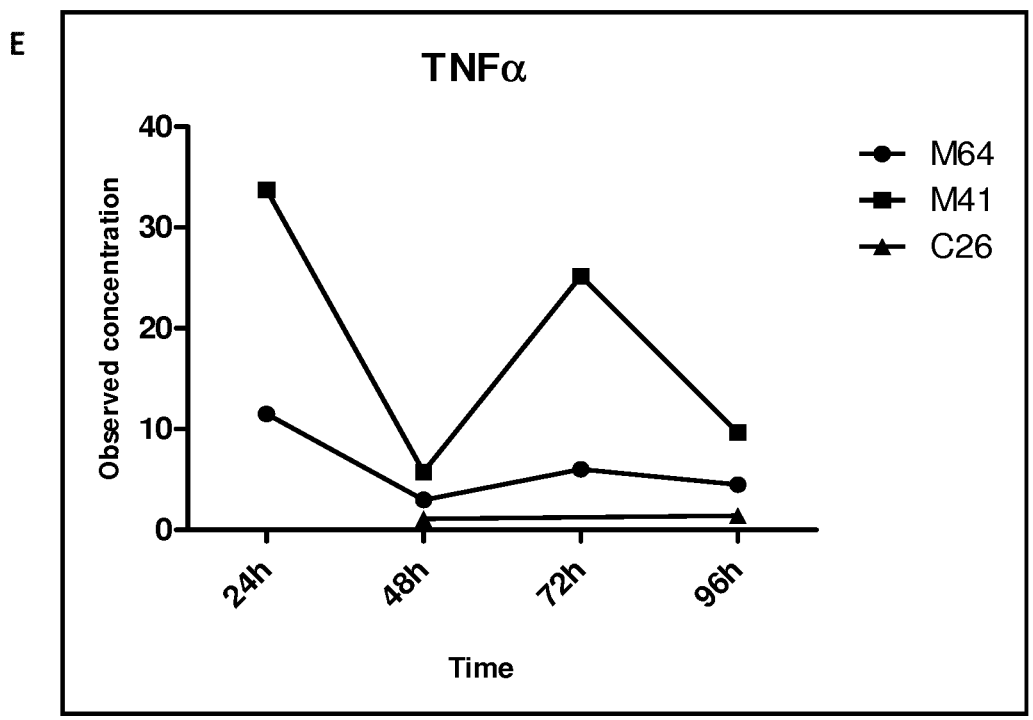

FIG. 7: Cytokine (ck) release profile of scDb redirected T-cells, as described in Example 3.

Figure 7F:
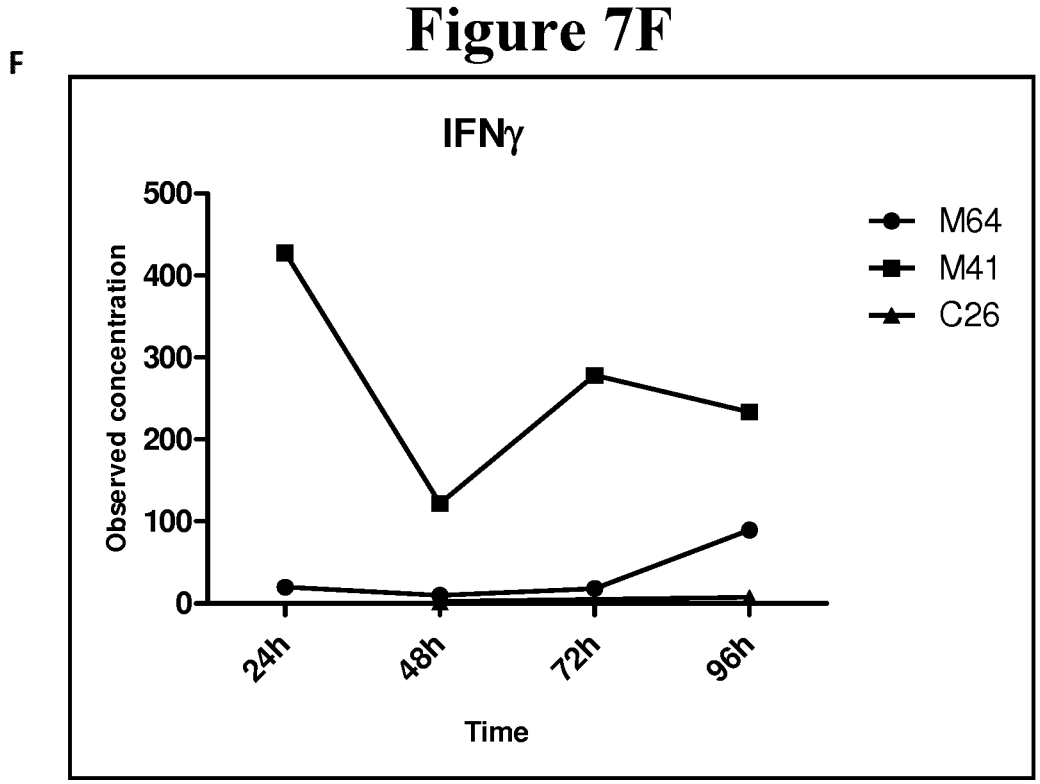
Figure 7G:
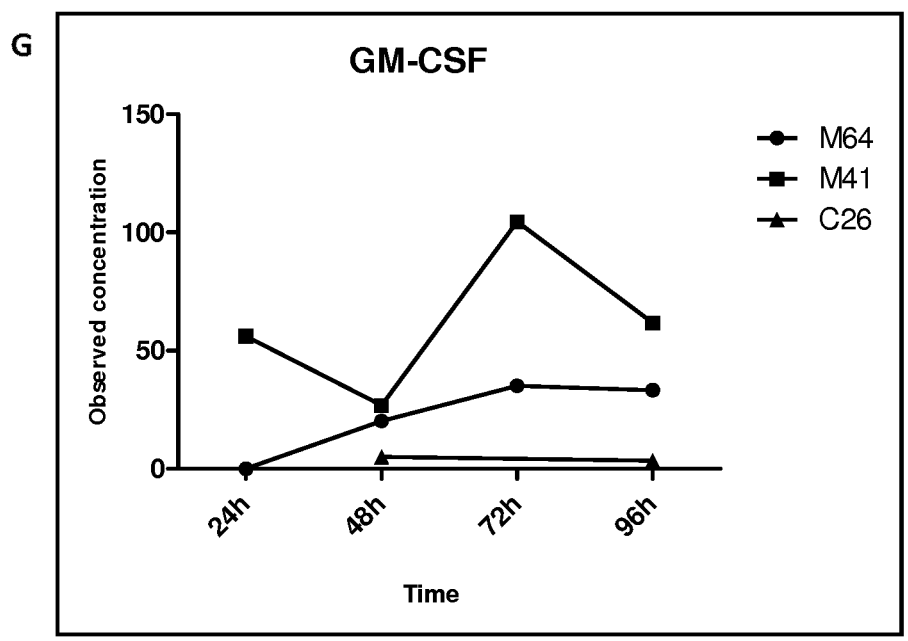
Figure 7H:
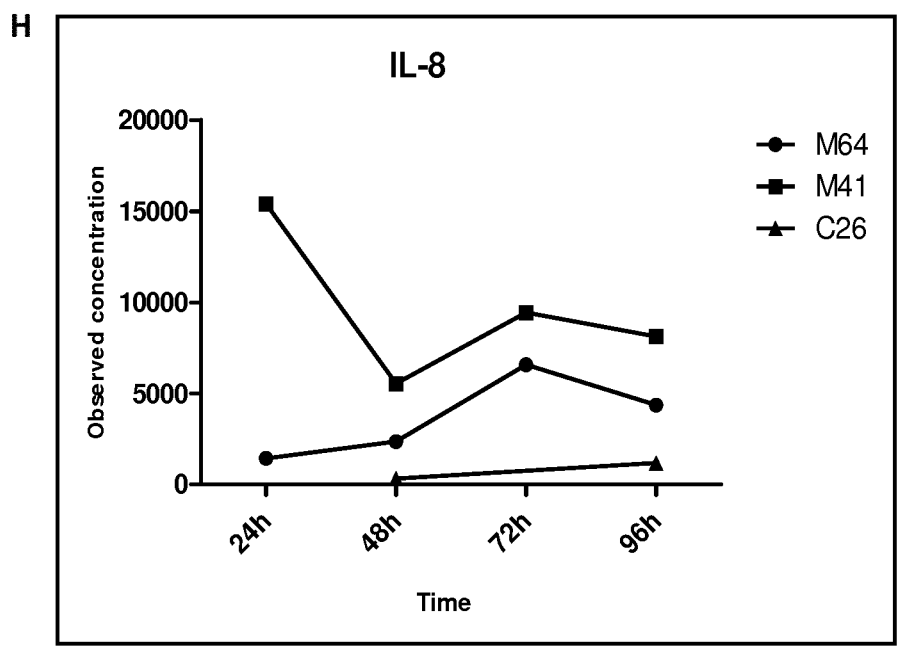

The medium of tumor cells, incubated with T-cells and with or without scDb, was picked daily for 4 days: the amount of IL-2 (FIG. 7A), IL-4 (FIG. 7B), IL-6 (FIG. 7C), IL-10 (FIG. 7D), TNFα (FIG. 7E), IFNγ (FIG. 7F), GM-CSF (FIG. 7G) and IL-8 (FIG. 7H) was measured using Bioplex. The mean value of duplicate wells is represented in each graph. Each point represents level of ck produced after treatment with scDb and T-cells subtracted of T-cell cytokine basal production when T-cells were incubated with only tumor cells.

DETAILED DESCRIPTION OF THE INVENTION

The present invention concerns novel bispecific antibodies in the scDb format which have the capability of binding both the TRAIL-R2 and the CD3 expressed on T-cells. Many therapies had been developed in the field of cancer immunotherapy, but these have not always been effective or have shown good results.

In fact, in most cases, after a preliminary remission or a stabilization of the disease, the tumor relapsed and this fact is particularly due to the arising of drug-resistance in tumor cells. In recent years, targeted therapy, in combination with chemotherapy, has shown to improve outcomes over chemotherapy alone. In particular a new class of therapeutics, the bispecific antibodies arose to be a useful tool in immunotherapy. Bispecific antibodies act retargeting immune cells to tumor ones to kill them.

The present invention regards a bispecific antibody able to bind TRAIL-R2 and the CD3 present on T-cells.

Among different constructs anti-TRAIL-R2/anti-CD3, only one showed good biochemical properties and biological activity. Using different methods we demonstrated that the BsAb can allow the formation of the immunocytolitic synapse between tumor cells and lymphocytes. After the formation of the synapse, we can observe T-cell (both CD4+ and CD8+) activation with up-regulation of CD69, CD137, PD-1 and CD25 and production of inflammatory cytokines without off target toxicity. After the formation of the synapse and the activation, T cells were able to lyse tumor cells derived from very different malignancies, like breast cancer, melanoma, ovarian cancer, prostate cancer, colorectal cancer, hepatocellular cancer and lung cancer. The same experiments performed on normal cells showed no T-cell activation resulting in the absence of cytotoxic events.

The invention therefore describes a single-chain bispecific diabody or fragments thereof comprising:

a. a variable domain of a heavy chain of an immunoglobulin (VH) with a first specificity (A) or fragments thereof, wherein said heavy chain ($VH_A$) variable domain has the amino acid sequence according to SEQ ID NO:1, or direct equivalents thereof, wherein the first specificity (A) is directed against the TRAIL-R2 antigen;

b. a variable domain of a light chain of an immunoglobulin (VL) with a second specificity (B), or fragments thereof, wherein said light chain ($VL_B$) variable domain has the amino acid sequence according to SEQ ID NO:3, or direct equivalents thereof, wherein the second specificity (B) is directed against a T lymphocyte CD3;

c. a variable domain of a heavy chain of an immunoglobulin (VH) with the specificity (B), or fragments thereof, wherein said heavy chain ($VH_B$) variable domain has the amino acid sequence according to SEQ ID NO:5, or direct equivalents thereof; and d. a variable domain of a light chain of an immunoglobulin (VL) with the specificity (A), or fragments thereof, wherein said light chain ($VL_A$) variable domain has the amino acid sequence according to SEQ ID NO: 7, or direct equivalents thereof; wherein the VH and VL domains of the single-chain multiple antigen-binding molecule are connected in the order $VH_A$-$VL_B$-$VH_B$-$VL_A$, wherein each VH and VL domain is connected with a peptide linker, wherein said peptide linker between the $VH_A$ and the $VL_B$ domains and between the $VH_B$ and the $VL_A$ domains consist of four Glycine amino acid residues and one Serine amino acid residue (GGGGS) as encoded by the nucleotide sequence of SEQ ID NO:22, and the peptide linker between the $VL_B$ and the $VH_B$ domains consists of three linker sequences consisting each of four Glycine amino acid residues and one Serine amino acid residue each (GGGGS)$_3$ (as set forth in SEQ ID NO:15).

The BsAb is active on different tumor cells such as melanoma, ovarian carcinoma, breast carcinoma, prostate carcinoma, colorectal adenocarcinomas, hepatocellular carcinoma and lung squamous carcinoma and joins the potential antitumor ability of TRAIL to the ability of bypassing resistance.

ScDb format derives from the diabody (Db) format. BsAbs, in Db format with an anti-CD3 moiety, demonstrated to be able to retarget efficiently T-cells to lyse tumors, including prostate cancer cells through the binding to the prostate specific membrane antigen (Buhler P. et al, Cancer Immunol immunother 2008, 57:43-52) and B cell lymphoma through the binding to the CD19 (Cochlovius B., et al., Journal of Immunology, 2000, 165: 888-895).

Despite in vitro encouraging results, Dbs encountered significant drawbacks that limited their use such as the reduced in vivo stability and the presence of inactive homodimers along with the functional heterodimers. These problems were overcome by introducing another peptidic linker of about 15 aa that connect the two polypeptide chains allowing the more efficient pairing between cognate variable domains, fusing the two antibody domains resulting in single-chain diabodies.

In the present invention:
the term "specificity" as used herein refers to the ability of recognizing a particular sequence or domain and refers to the capability of binding that sequence or domain;
the term single-chain bispecific antibody (scBsAb) refers to a multiple antigen-binding molecule which has two arms: the anti-TRAIL-R2 arm, that binds TRAIL-R2 and mimics the pro-apoptotic potential of soluble TRAIL, and the anti CD3 arm which retargets T cells on tumor ones and kills the tumor cells. The BsAb according to the present invention is in the scDb;
the term "fragment thereof" as used herein refers to single chain antibody fragments which have smaller size with respect to the corresponding antibody.

The single-chain bispecific antibody or fragments thereof according to the present invention is in the scDB format, which advantageously has a more compact form in comparison to other bispecific antibody formats and allows the formation of immunocytolytic synapses. The same antibody variable domains organized/assembled in BiTE-like format are not functional.

Figure 2:
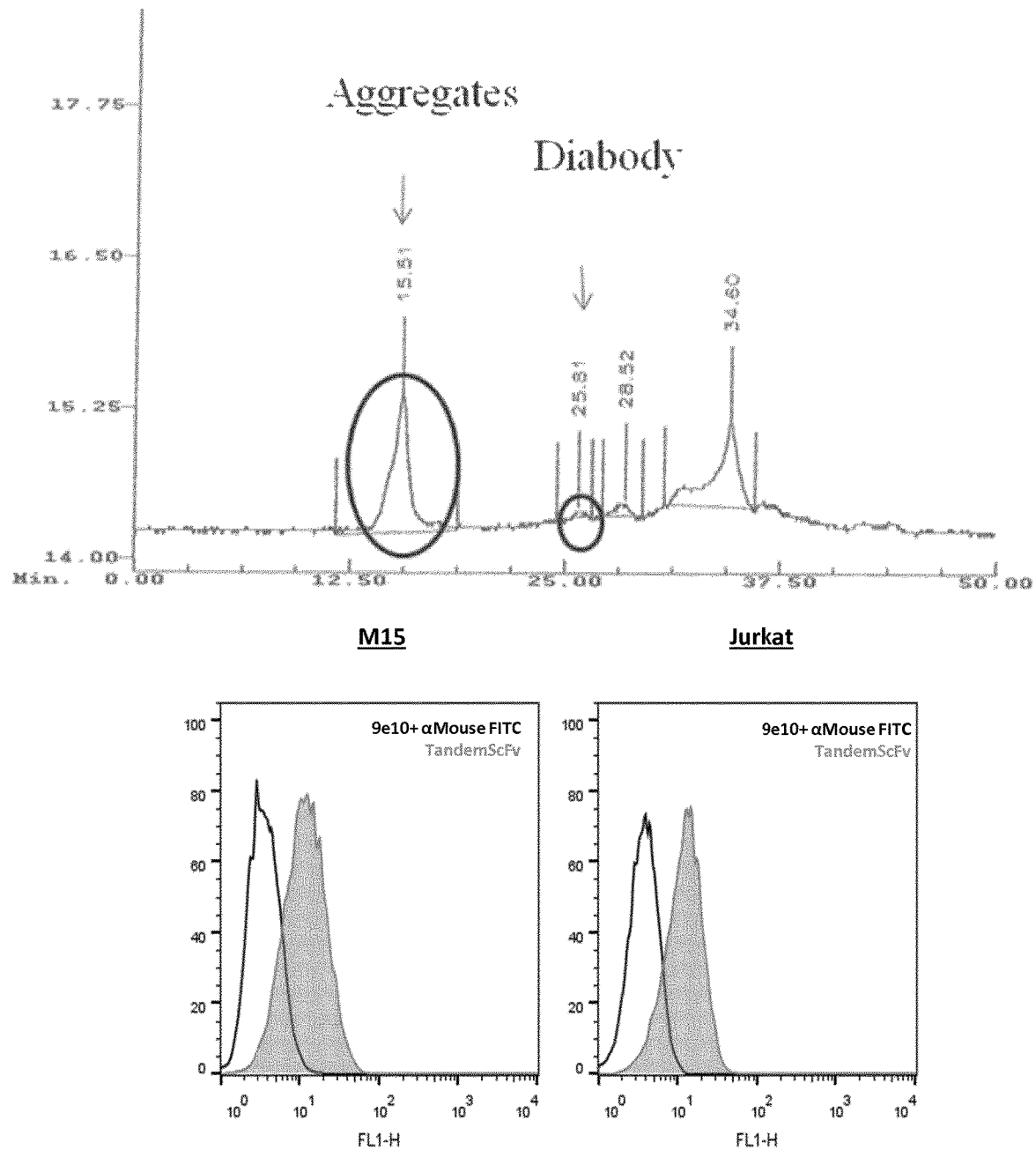
FIG. 2: shows the comparison of results of a size exclusion chromatography profile between the BsAb 16e2/TR66 in the BITE-like conformation and those obtained with a scDb 16e2/hUCTH1, according to the invention, as described in Examples 2 and 3. The binding ability was assessed by FACS on cells expressing or not expressing TRAIL-R2 and CD3. Empty peak: negative control; grey peak: scDb plus anti-Tag and anti-mouse antibodies.
Figure 2:
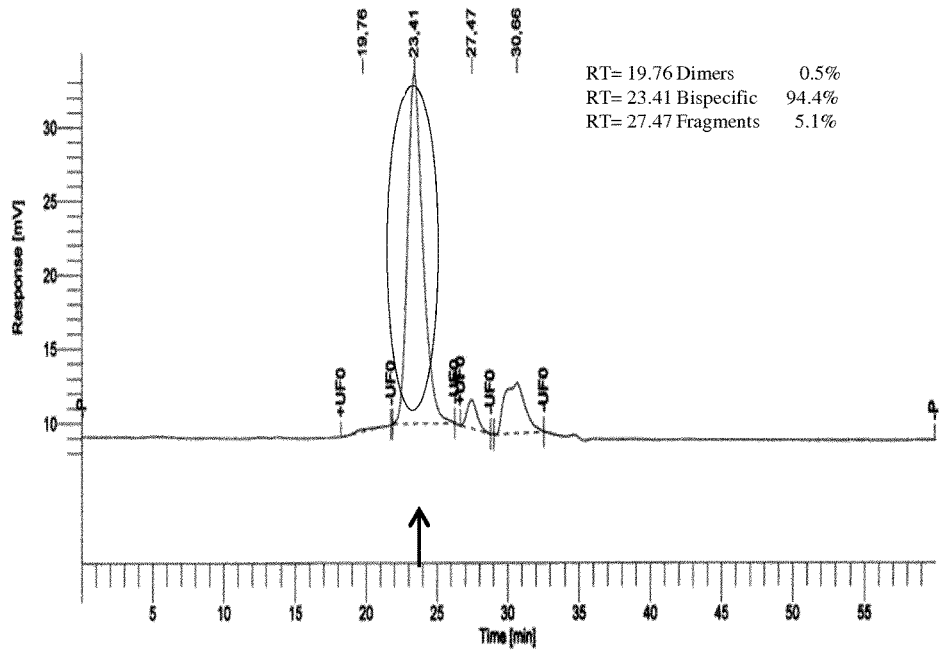
Figure 2:
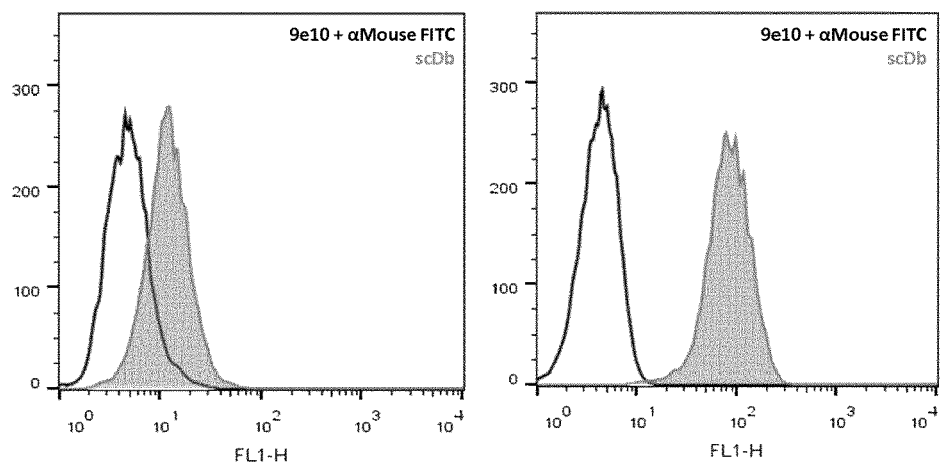
Figure 2:
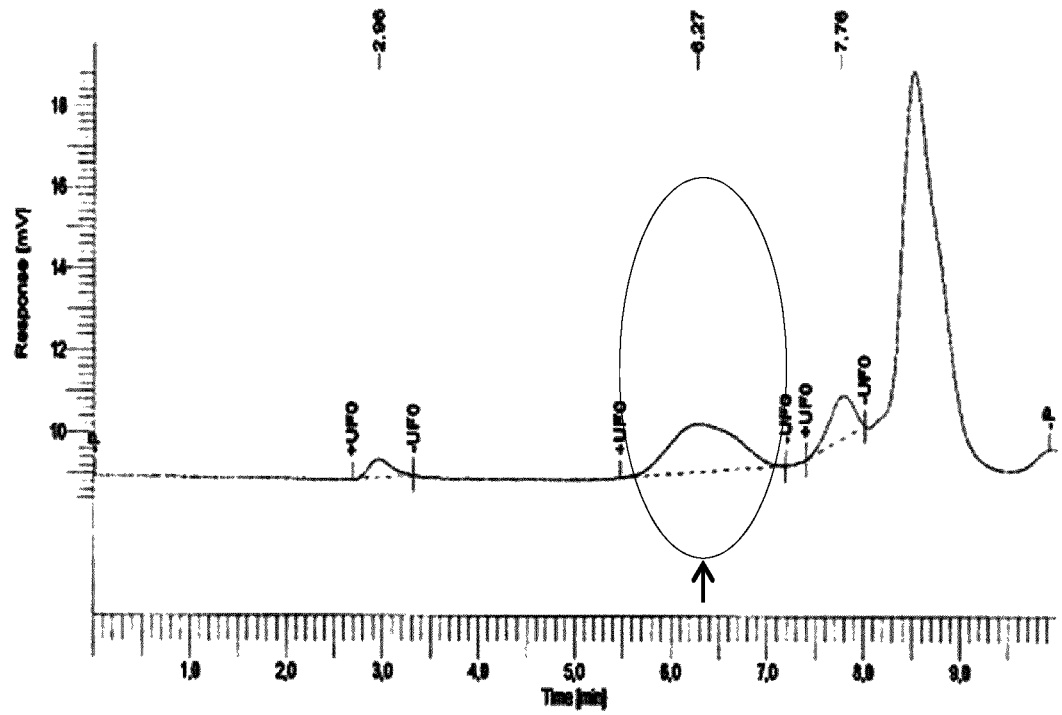
Figure 2:
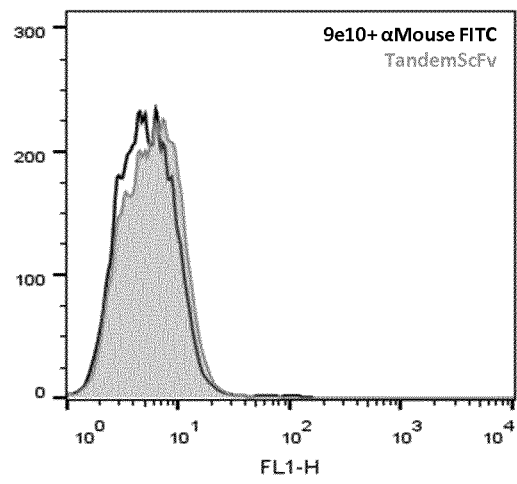
Figure 2:
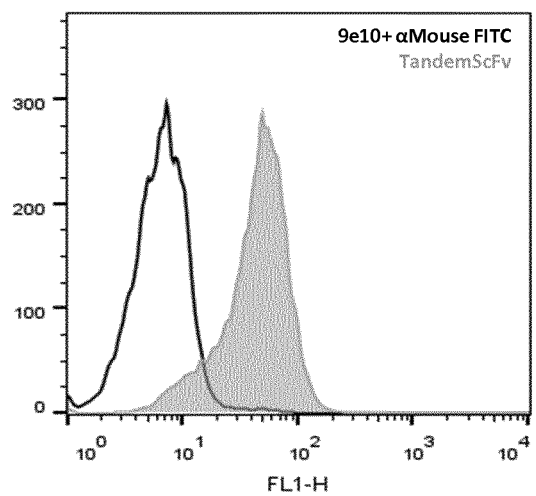
Figure 2:
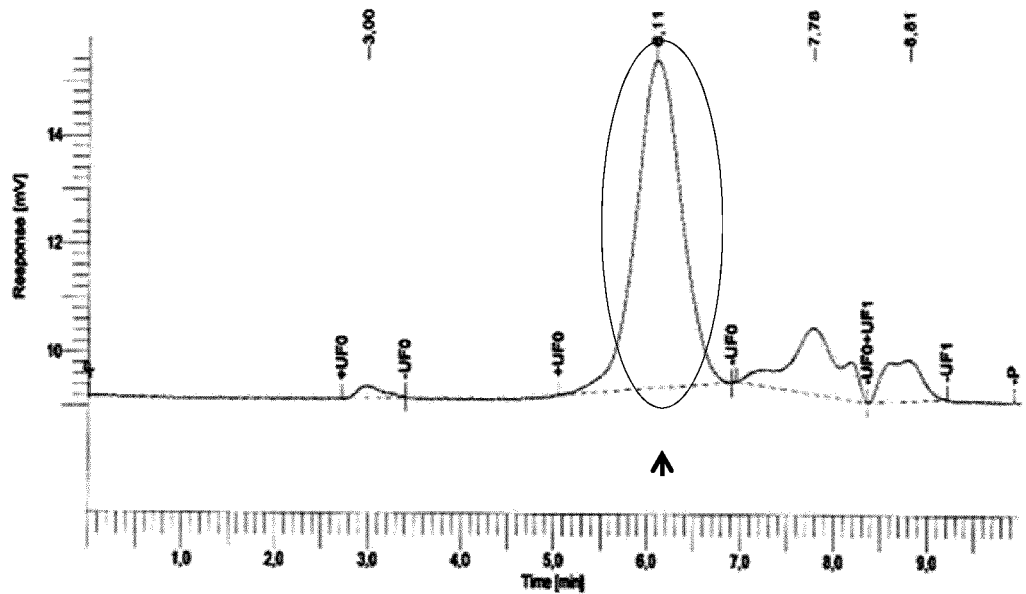
Figure 2:
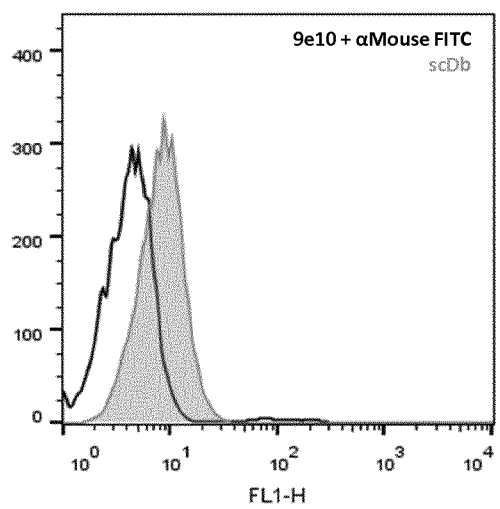
Figure 2:
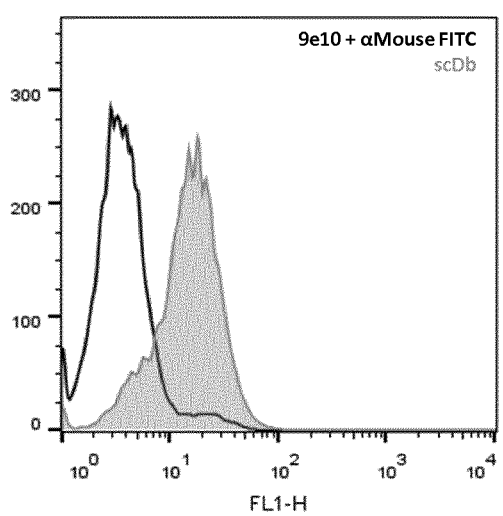

The results described in Example 3 and shown in FIG. 2 indicate that the tandem scFv BsAb 16e2/TR66 which is in the BITE-like format loses its capability of binding only after 2 days. Without being bound to any theory, this could be due to the instability of the structure that had the tendency to aggregate like demonstrated by the size exclusion chromatography profile.

On the contrary, the scDb 16e2/hUCTH1 according to the invention, which is in the diabody format, surprisingly was stable and the aggregates did not exceed 0.5% also after 2 years (FIG. 2B). Using the same variable regions (16e2 and hUCTH1) but converting the BsAb in Tandem scFv format, it can be noticed that the construct never recognizes the TRAIL-R2 but only the CD3 (FIG. 2C). We also built a scDb using as anti-TRAIL-R2 Drozitumab a derivative of the 16e2 that varies from 16e2 only in few aminoacids and as anti-CD3 the hUCTH1. Also in this case the construct works only for few days.

In a further aspect, the invention provides a single-chain bispecific antibody or fragments thereof, wherein said direct equivalents have at least 95% overall sequence homology/identity with said variable domains.

The direct equivalents of the VH and VL variable domains according to the present invention have at least 96%, 97% 98% or 99% overall sequence similarity or homology.

In a preferred invention the single-chain bispecific antibody or fragments thereof, has the amino acid sequence according to SEQ ID NO: 13, and is also referred to as "scDb 16e2/hUCHT1" or direct equivalents thereof. The BsAb according to the present invention is also for example represented in FIG. 1C, which reports an example of the sequence in which the $V_H$ and $V_L$ domains are connected.

In one aspect, an example of BsAb according to the invention is in the following sequence:
the $VH_A$ domain, followed by a linker sequence consisting of four (4) Glycine amino acid residues and one (1) Serine amino acid residue (GGGGS) as encoded by the nucleotide sequence of SEQ ID NO:22, the $VL_B$ domain, followed by three (3) linker sequences consisting each of four Glycine amino acid residues and one Serine amino acid residues each ((GGGGS)$_3$) corresponding to SEQ ID NO:15), followed by the $VH_B$ domain, followed by a linker sequence consisting of four (4) Glycine amino acid residues and one (1) Serine amino acid residue (GGGGS) as encoded by the nucleotide sequence of SEQ ID NO:22 and the $VL_A$ domain.

In a further aspect, an example of BsAb according to the invention has linkers and domains in the following sequences: SEQ ID NO:22, SEQ ID NO:2, SEQ ID NO:10, SEQ ID NO:4, SEQ ID NO:11, SEQ ID NO:6, SEQ ID NO:12, SEQ ID NO:8, terminal linker nucleotide sequence GCGGCCGC.

The linker sequences can include a restriction enzyme site for cloning purposes, but the person of skill in the art can easily understand that such restriction sites may be modified according to the researcher's need, and that the linker sequences are not limited to a particular restriction site.

In a preferred embodiment, the present disclosure provides a BsAb having the amino acid sequence of SEQ ID NO 13, and a nucleotide sequence of SEQ ID NO: 21.

In a second aspect thereof, this invention moreover provides a composition comprising a single-chain bispecific antibody molecule or fragment thereof, according to the present invention and a labelling agent.

In a preferred aspect, the composition according to the invention, comprises a labelling agent chosen from the group consisting of a radionucleotide, fluorescent nanoparticles or any methods capable of multimerizing the BsAb (such as, biotin tag or leucine zipper) according to the present invention.

In a further aspect of the present invention is a pharmaceutical composition comprising a single-chain bispecific antibody molecule or fragment thereof, according to the present invention and a pharmaceutically acceptable carrier.

The pharmaceutical composition according to the invention is for topical, intramuscular, intravenous infusion, subcutaneous, or other administration routes.

The pharmaceutical composition provided can be used in combination with at least one further compound which is able to enhance or reduce its efficacy. Examples of compounds which are able to enhance or reduce the efficacy of the pharmaceutical composition according to the invention include TRAIL sensitizers that are included in the group of Anthracyclines (such as Doxorubicin), HDAC inhibitors (e.g.

Suberoylanilide Hydroxamic Acid), CDK inhibitors (e.g. Flavopiridol), ER inhibitors (e.g. Tamoxifen), Bcl-2 inhibitors (e.g. ABT-737), Smac mimetics (e.g. LBW242), carbo- or cis-platin, irinotecan, bortezomib.

According to another aspect, the described invention provides a method for redirecting the cytotoxic action of the T-lymphocytes on a tumor cell, comprising the step of by contacting said tumor cell with the single-chain bispecific antibody as disclosed herein.

According to another aspect, the described invention provides a single-chain bispecific antibody or fragment thereof, according to the present invention, for use in the treatment of a tumor.

In a preferred aspect, the single-chain bispecific antibody or fragment thereof, according to the present invention is for use in the treatment of a tumor, wherein said tumor is selected from the group consisting of melanoma, ovarian carcinoma, breast carcinoma, prostate carcinoma, colorectal adenocarcinomas, hepatocellular carcinoma and lung squamous carcinoma.

Advantageously the ScDb according to the present invention can be used in the treatment of all TRAIL-R2 positive tumors deriving from different organs and at different stages and grades.

In a preferred aspect, the single-chain bispecific antibody or fragment thereof, according to the present invention is for use also in the treatment of patients which are resistant or intolerant to previous treatment with at least one antitumor agent or wherein the treatment with an antitumor agent should be avoided. This gives a further chance of treatment for those patients that are resistant or become resistant to other treatments Furthermore, the single-chain bispecific antibody or fragment thereof, according to the present invention is for the treatment which is prophylactic or therapeutic.

For the purposes of the present invention, each single-chain bispecific antibody domain or linker has a corresponding SEQ ID NO. as follows:

SEQ ID NO:1 corresponds to the amino acid sequence of a variable domain of a heavy chain of an immunoglobulin (VH): $VH_A$ 16E2 (Class IGHV 3-20*01);

SEQ ID NO. 2 corresponds to the nucleotide sequence of a variable domain of a heavy chain of an immunoglobulin (VH): $VH_A$;

SEQ ID NO. 3 corresponds to the amino acid sequence of a variable domain of a light chain of an immunoglobulin (VL): $VL_B$ (hUCTH1);

SEQ ID NO. 4 corresponds to the nucleotide sequence of a variable domain of a light chain of an immunoglobulin (VL): $VL_B$;

SEQ ID NO. 5 corresponds to the amino acid sequence of a variable domain of a heavy chain of an immunoglobulin (VH): $VH_B$ (hUCTH1);

SEQ ID NO. 6 corresponds to the nucleotide sequence of a variable domain of a heavy chain of an immunoglobulin (VH): $VH_B$;

SEQ ID NO. 7 corresponds to the amino acid sequence of a variable domain of a light chain of an immunoglobulin (VL): $VL_A$ of 16E2 (Class IGLV3-19*01);

SEQ ID NO. 8 corresponds to the nucleotide sequence of a variable domain of a light chain of an immunoglobulin (VL): $VL_A$;

SEQ ID NO: 9 (sequence which comes before VHA domain, Sfi I restriction site)

SEQ ID NO: 10 (linker between $VH_A$ and $VL_B$ domains, Age I restriction site)

SEQ ID NO: 11 (nucleotide sequence encoding_linker between $VL_B$ and $VH_B$ domains, $(GGGGS)_3$ linker)

SEQ ID NO: 12 (linker between $VH_B$ and $VL_A$ domains, Xba I restriction site) Sequence of terminal linker: GCG-GCCGC (terminal linker, after $VL_A$ domain, Not I restriction site)

SEQ ID NO: 13 corresponds to the amino acid sequence of the single-chain bispecific antibody scDb 16e2/hUCTH1

SEQ ID NO. 14 corresponds to the nucleotide sequence of the single-chain bispecific antibody scDb 16e2/hUCTH1 with an upstream sequence which was used to clone the scDb in the vector.

SEQ ID NO. 15 corresponds to the amino acid sequence of the alternative linker between VLB and VHB domains SEQ ID NO. 16 corresponds to the amino acid sequence of the single-chain bispecific antibody with His and Myc tags SEQ ID NO. 17 corresponds to the amino acid sequence of Clone 7 anti-TRAIL-R2 ScFv isolated with Phage Display SEQ ID NO. 18 corresponds to the amino acid sequence of Clone 8 anti-TRAIL-R2 ScFv isolated with Phage Display SEQ ID NO. 19 corresponds to the amino acid sequence of Clone 44 anti-TRAIL-R2 ScFv isolated with Phage Display SEQ ID NO. 20 corresponds to the amino acid sequence of Clone 56 anti-TRAIL-R2 ScFv isolated with Phage Display SEQ ID NO. 21 corresponds to the nucleotide sequence of the single-chain bispecific antibody scDb 16e2/hUCTH1 (BsAb)

SEQ ID NO. 22 corresponds to the nucleotide sequence of the (GGGGS) linker

Various embodiments and aspects of the present invention as delineated hereinabove and as claimed in the claims section below find experimental support in the following examples.

EXAMPLES

Reference is now made to the following examples, which together with the above description illustrate some embodiments of the invention.

Cell Lines

M41, M15 and M64 human melanoma cells were used. M15, M64 and M41 are cells that have different TRAIL-R2 expression and sensitivity to sTRAIL treatment: in particular, M15 are sTRAIL-sensitive and high-expression; M41 are sTRAIL partially sensitive and high expression while M64 are resistant with low expression.

HeLa (cervix epithelial adenocarcinoma), A431 (epidermoid epithelial carcinoma), SKOV3, A2774, A2780 and NL3507 INT-Ov-11 (epithelial ovarian carcinomas), MDA-MB-231 and MT-3 (breast cancer triple negative), LnCAP, DU145 and PC3 (prostate carcinoma), CaCo2 (colorectal adenocarcinomas), HepG2 (hepatocellular carcinoma), SkMes (lung squamous carcinoma), HEK-293 (normal embryonic kidney), Jurkat (immortalized line of human T lymphocytes) and MDA-MB-468 (breast cancer triple negative, TRAIL-R2 negative cell line) SU-DHL-4 (lymphoma) were purchased from American Type Culture Collection (Manassas, Md.). INT-Ov-11 (epithelial ovarian carcinoma) was developed by our group.

Hybridoma producing the mAb the anti-myc tag mAb 9E10 (CRL-1729) was purchased from ATCC.

Bacterial Strains.

*Escherichia coli* strains. TG1 {supEthi-1 ((lac-proAB) hsd (5[F' traD36+proAB+laclq lacZ(M15)]} was used for antibody phage display panning and HB2151 {nalr thi-1 ara lac-proAB [F' proAB+laciq lacZ(M15)]} was used for soluble production of the bispecific antibody.

Example 1

Isolation of Single-Chain Antibody Fragments (Single-Chain Variable Fragment scFv) Against TRAIL-R2

Three cycles of enrichment were performed to isolate scFv against TRAIL-R2 as described below. The titer of the eluted phages increased gradually after each cycle and the binding of produced phages was tested in Phage ELISA and increased proportionally with the enrichment 768 randomly picked colonies, derived from phages after enrichment, were tested in single clone phage ELISA and 4 clones, specific to naïve TRAIL-R2, were isolated, sequenced and characterized. The 4 scFvs were produced in soluble form and resulted capable of specifically binding TRAIL-R2+ cells.

Materials and Methods:

Antibody Phage Display

ScFvs directed against TRAIL-R2 were isolated using Phage Display antibody technique. A pre-made human ScFv phage display library (proprietary) was used and 3 rounds of selection were performed. For selection on naïve TRAIL- R2, 6×10⁶ lymphoma SU-DHL-4 receptor-positive cells were lysated. The TRAIL-R2 protein, contained in the lysate, was captured with mouse anti-human TRAIL-R2 antibody (R&D Systems) previously conjugated to DYNA-BEADS® M-280 sheep anti-mouse IgG (Life Technologies). TRAIL-R2 trapped with magnetic beads was incubated in MPBS (milk 4%+PBS) in agitation for one hour and after the phage library was added and incubated for two hours at room temperature in agitation and washed with PBST (PBS and Tween 0.1%) for 20, 15 and 10 times respectively in the first, second and third cycle of enrichment. After the washing step, phages that displayed antibody fragment specific for the receptor, remained attached to the beads and were used to infect 2 ml of TG1 E. Coli grown at an O.D. of 0.4-0.5 in 2×TY medium. Infected bacteria were plated on 2×TYE+100 µg/mL ampicillin in a square plate dish (100×15 mm) and grown at 30° C. O/N (overnight). Colonies were counted, screened by PCR and the plate was scraped. To produce phages for the successive round, 50 µl of scraped bacteria were inoculated in 50 ml of 2×TY medium with 1% glucose and ampicillin (100 mg/ml). When O.D. reached 0.4-0.5, bacteria were infected with 5×10⁵ pfu M13KO7 helper phage (New England Biolabs) for 30 minutes at 37° C. in a thermostatic bath. Bacteria were then centrifuged and resuspended in the same medium without glucose and grown at 30° C. O/N. Phages were PEG-precipitated, resuspended in PBS and titrated before their use for the successive round of selection. After the third round phages were tested in FACS to evaluate TRAIL-R2 binding capability. With single colonies derived after the enrichment, single phage ELISA was performed.

Single Clone Phage ELISA.

After the third round of selection, phage-infected bacteria were plated on 2×TYE+ampicillin plates. Production of single clone phages was performed, as described above, in each well of a deep 96-well plate. To test the binding capability of supernatant of each well single phage Elisa was performed. 96-well ELISA plate with anti-TRAIL-R2 (R&D Systems) was coated O/N at 4° C. After 3 washes with PBS-Tween 0.1% and PBS, 0.5 µg of SU-DHL-4 lysate was incubated for 1 h at room temperature. The presence of specific clones was revealed with anti-M13 HRP antibody.

Antibody Fragment Soluble Expression.

Soluble bispecific antibodies or antibody fragments were produced in E. Coli. Competent HB2151 E. Coli were freshly transformed, plated on 2×TYE and grown O/N at 37° C. One single colony was inoculated and grown in 2×TY (0.1% glucose and 100 µg/mL ampicillin) medium overnight at 37° C. The following day, the culture was inoculated in fresh medium starting from an OD of 0.1 and bacteria were grown until the culture reached an OD of 0.8-0.9. The culture was centrifuged and the exhaust medium was changed with fresh medium specific for the induction of the soluble protein (2×TY+0.1% glucose+100 µg/mL ampicillin+1 mM IPTG). To allow an efficient soluble protein expression, bacteria were incubated O/N at the temperature that was optimal for each protein (25-30° C.). The following day, bacteria were collected by centrifugation and an osmotic shock treatment protocol, using 200 mM Tris buffer pH 7.5 containing 1 mM EDTA and 20% sucrose for 1 hour at 4° C. in agitation, was performed to extract periplasmic proteins containing the bispecific antibody or antibody fragment.

Periplasmic preparations were purified using IMAC protocol with Nickel or L protein chromatography column.

Example 2

Construction of Bispecific Antibodies

Figure 1A:
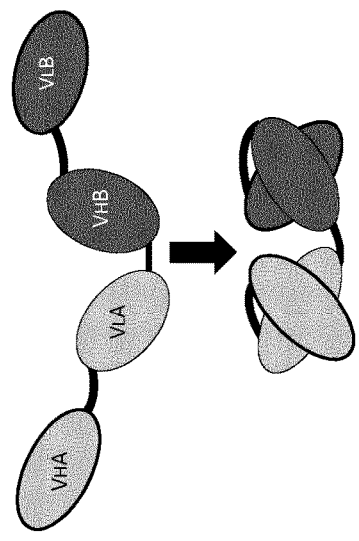
FIG. 1A: Tandem scFv BsAb format: anti-TRAIL-R2 scFv (pale grey) joined by a short linker to anti-CD3 scFv (dark grey) (derived from TR66 or hUCTH1)

We used the variable domains of the 4 isolated anti-TRAIL-R2 scFvs described in Example 1, and we associated them with the variable domains of one of the two murine anti-CD3 hybridomas described below (TR66 and OKT3) to build bispecific antibodies in tandem ScFv format (SEQ ID NOs 17, 18, 19 and 20). The structure of the bispecific antibody was composed by the two scFvs, the first anti-TRAIL-R2 and the second anti-CD3, joined by a short GGGGS linker as encoded by the nucleotide sequence of SEQ ID NO:22 that confers rigidity to the structure and doesn't allow the mismatched pairs of variable domains of different specificities (FIG. 1A). One of these clones, clone 8 (SEQ ID NO; 18), in pairing with TR66 scFv as Tandem ScFv format, showed the best binding capability. By FACS on NHL, HeLa and Melanoma cell lines with different expression of TRAIL-R2 the BsAb demonstrate a good reactivity similar to the entire IgG bivalent positive control despite its monovalent binding. Unfortunately, the BsAbs demonstrated a poor stability during time probably due to the presence of aggregates as demonstrated by Size Exclusion Chromatography (SEC).

To find a more stable clone we random mutagenized clone 8 and the pool of the mutated scFvs was cloned in a vector containing TR66 scFv. Single clone ELISA was performed to isolate clones with better binding on positive cells. Of 90 clones, two, C2 and C3, give good binding and specificity. Their sequences demonstrate that they have 2 and 1 point mutations in the frameworks respectively. More precisely, in C2 there is 1 amino acid change in framework 1 and 1 in framework 2 of the VH and, in C3 there is 1 amino acid change in framework 1 of the VL. The stability was in any case not yet sufficient for our purposes.

In parallel we decided to start with the selection of a library directly in BiTE-like BsAb format: different types of linker can influence binding and properties of scFv fragments and the scFv can have different behavior if assembled as BsAb. The pool of fragments obtained after the 2$^{nd}$ panning of the naive scFv library, from which we selected the above described clones, was cloned in a vector containing the scFv of TR66. Also a construct, containing a well characterized anti-TRAIL-R2 clone 16e2, was generated and produced to be used as a positive control. The library obtained was transiently heated to induce unfolding and to promote aggregations. After cooling phage display antibody fragments that unfold reversibly where thereby enriched with respect to those that do not. After two rounds of selection 6 of the 90 clones were found positive in ELISA on melanoma cells and negative on a cell line not expressing TRAIL-R2 (MDA-MB-468). These 6 clones were further analyzed by FACS and three of them demonstrated good binding on both arms. Also clones containing 16e2 scFv was able to specifically bind TRAIL-R2 and CD3 but like the other 6 clones, it maintained the specificity for at least 1 week and after the binding was lost probably due to the presence of aggregates as demonstrated by Size Exclusion Chromatography (SEC) (FIG. 2A).

TABLE 1

Different constructs produced and problems encountered

| Construct | Stability | Problems encountered |
|---|---|---|
| Tandem ScFv 16e2/TR66 | Stable for 5-7 days | Presence of aggregates |
| Tandem ScFv 16e2/hUCTH1 | Not stable | Presence of aggregates |
| scDb 16e2/hUCTH1 | Stable | NO aggregates |
| scDb Droz/hUCTH1 | Stable for 1 day | Difficulty in production/ Loss of functionality |
| scDb 16e2 -1mut/hUCTH1 | Stable for 2-3 days | Presence of aggregates |
| scDb 16e2 -2mut/hUCTH1 | Stable for 2-3 days | Presence of aggregates |
| Tandem ScFv and ScFvs containing different isolated anti-TRAIL-R2 variable domains and hUCTH1 or TR66 anti-CD3 domains | Not stable | Difficulty in production\purification Presence of aggregates |

Materials and Methods:
Bispecific Antibody in Bite-Like Format Construction.

For our purposes the isolated single-chain Fv fragments directed against TRAIL-R2 was joined by a flexible GGGGS linker as encoded by the nucleotide sequence of SEQ ID NO:22 to anti CD3 scFv. The anti-CD3 scFvs used were derived from two mouse hybridomas TR66 and OKT3. The antibody genes were cloned in pIT2 vector that contains, after the bispecific cassette gene, both an exahistidine and a Myc tags. Bispecific antibodies were expressed in HB2151 E. Coli and purified as described in Example 1.

Amplification Vh and Vl derived from second panning anti TRAIL-R2 Plasmids from phages derived after two panning cycles on naïve TRAIL-R2 were isolated using Wizard® Plus SV Minipreps DNA Purification (Promega). Using a pool of primers specific for all the Vh and Jk germ lines, the scFvs were amplified by PCR and were cloned, in the pIT2 vector that contains TR66 scFv through primer encoded SfiI/NotI sites, to generate a bispecific antibody library. This library was screened against natural TRAIL-R2 immobilized on magnetic beads using anti-TRAIL-R2 commercial antibody.

Binding Specificity of the Recombinant Antibody: FACS.

In all the experiments, $2 \times 10^5$ cells were incubated with primary antibody in PBS containing 1% of saturating FCS for 30 minutes at 4° C. BsAbs were detected using an anti-Histydine Tag antibody and anti mouse IgG (H+L specific) Alexa 488 labeled. Mouse anti-human TRAIL-R2 (R&D Systems) and mouse TR66 mAb, derived from Hybridoma, were used like positive controls. Fluorescence labeling was measured using FACS Calibur instrument (Becton Dickinson, Heidelberg, Germany). Data analysis was performed using FlowJo software (Tree Star Inc).

Example 3

New Format

Figure 1B:
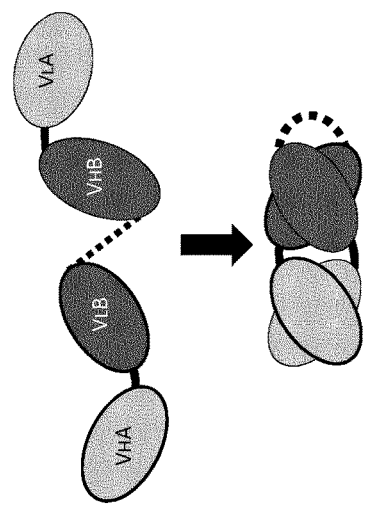
FIG. 1B: Bispecific scDb format: anti-TRAIL-R2 variable domains are at the extremities of the structure and are joined to anti-CD3 scFv by two identical 5 amino acids short linkers which avoid the formation of mismatched pairs.
Figure 1C:
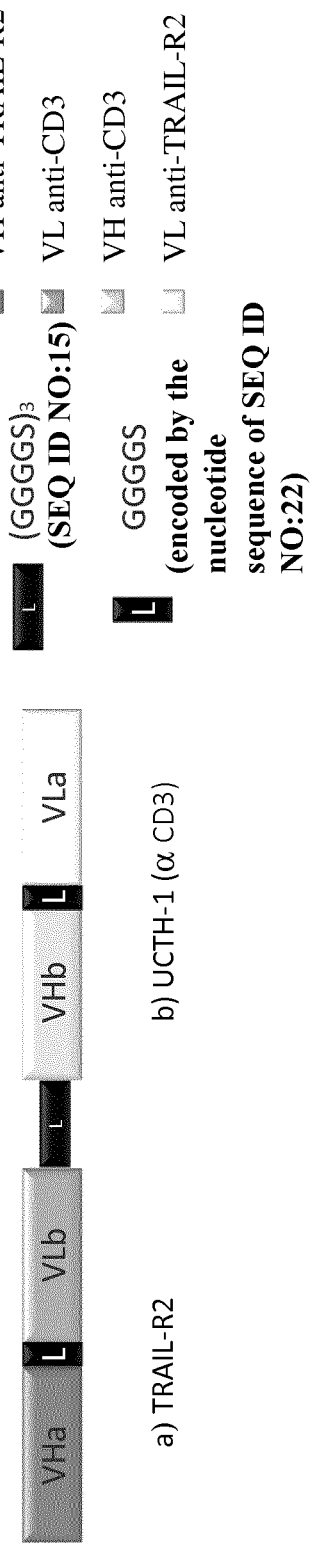
FIG. 1C: Cartoon representation of the Bispecific scDb construct.

The lack of stability in BiTE-like format induced us to construct the bispecific antibodies in a different format. A compact format, that allows the adjacency of T- and tumor cells necessary for immunocytolytic synapsis, is the single chain Bispecific Diabody (scDb). Bispecific diabody format (FIG. 1B) is composed by two scFvs in which the C-terminus of a VH domain is connected to the N-terminus of a VL domain of another specificity using a short rigid linker to restrict intra-chain pairing of VH and VL. In the scDb format, another linker $(GGGGS)_3$ (as set forth in SEQ ID NO:15) between the two chains stabilize the structure. We constructed scDbs with the sequence of the variable domains of all the isolated anti-TRAIL-R2 scFvs, 16e2 or Drozitumab (Genentech) and with the humanized antibody UCTH1 (hUCTH1) for the anti-CD3 specificity. The scFv of hUCTH1 has been used in many BsAb constructs and demonstrated to be stable when used joined with 16e2 to form a scDb.

Constructs were cloned in the pIT2 plasmid that allows the secretion of the scDb in bacteria HB2151 periplasm after induction with IPTG. The produced BsAbs have at the C-terminal two sequences which code respectively for a c-myc and an exahystidine tags. His-tag was inserted to allow the BsAbs purification using IMAC protocol.

Among all differently produced constructs in bispecific Tandem scFv or in scDb formats, we noted that low yield of production, lack of binding and/or presence of aggregation preclude the possibility to have a stable reagent except for scDb constructed with 16e2 and hUCTH1.

All the constructs had a very low production yield in comparison to 16e2×hUCTH1 scDb. The yield of standardized production is of about 50-100 µg/L while for the scDb is about 1-2 mg/L. To exclude that the difference of production yield is not due to chance, about 20 different production attempts were performed and results were comparable.

It can also be observed that 16e2×hUCTH1 TaScFv could not bind TRAIL-R2 specificity (FIG. 2C), and that other constructs like Drozitumab×hUCTH1 scDb (FIG. 2D) or 16e2×TR66 TaScFv (FIG. 2A), were capable of binding both the specificities immediately after production, but lost the TRAIL-R2 or CD3 binding ability respectively, after 1-3 days storage Investigating the cause of this loss of binding, a size-exclusion chromatography (SUPEROSE 12 10/300) (range separation: 300 Kd-10 Kd; GE Healthcare) assay was performed and aggregation of the 16E2×TR66 TaScFv that occurred in the 16 hours after purification was observed. The 16E2×hUCTH1 scDb format was superior compared to the other constructs with no aggregation tendency and preservation of binding affinity towards both specificities, TRAIL-R2 and CD3, also after a two year storage (FIG. 2B).

Single Chain Diabody Characterization

Figure 3:
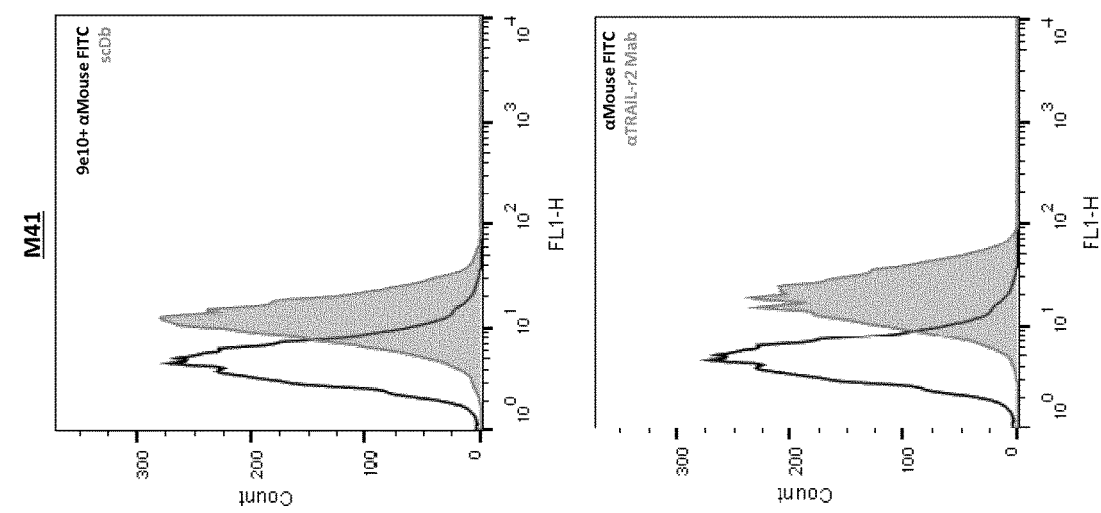
FIG. 3 Functional and biochemical analysis of scDb 16e2/hUCTH1, as described in Example 3.
Figure 3A:
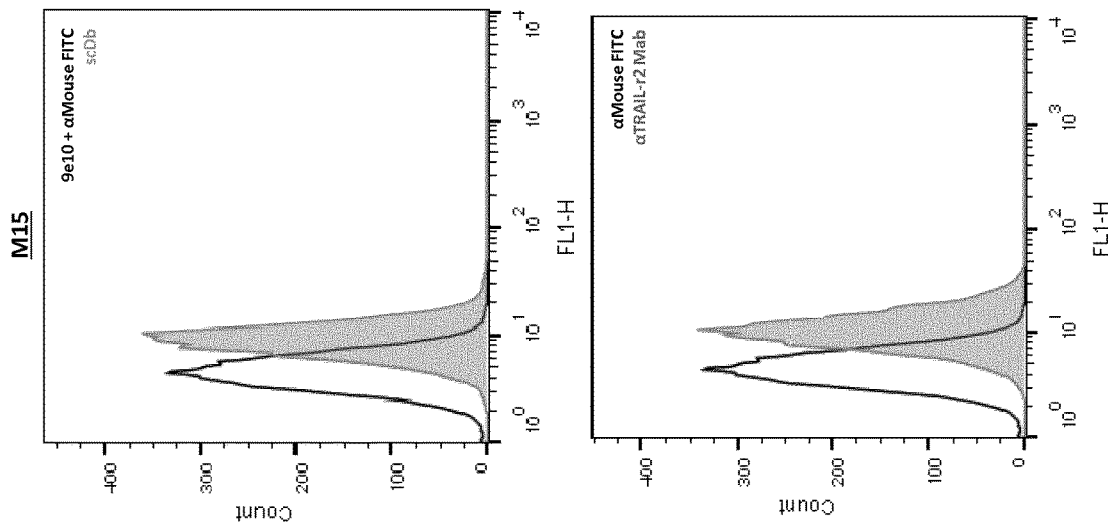
FIG. 3A: Flow cytometric analysis performed on a panel of TRAIL-R2$^+$ melanoma cell lines with different receptor expression levels, on CD3$^+$ Jurkat and on TRAIL-R2$^-$\CD3$^-$ MDA-MB-468.
Figure 3A:
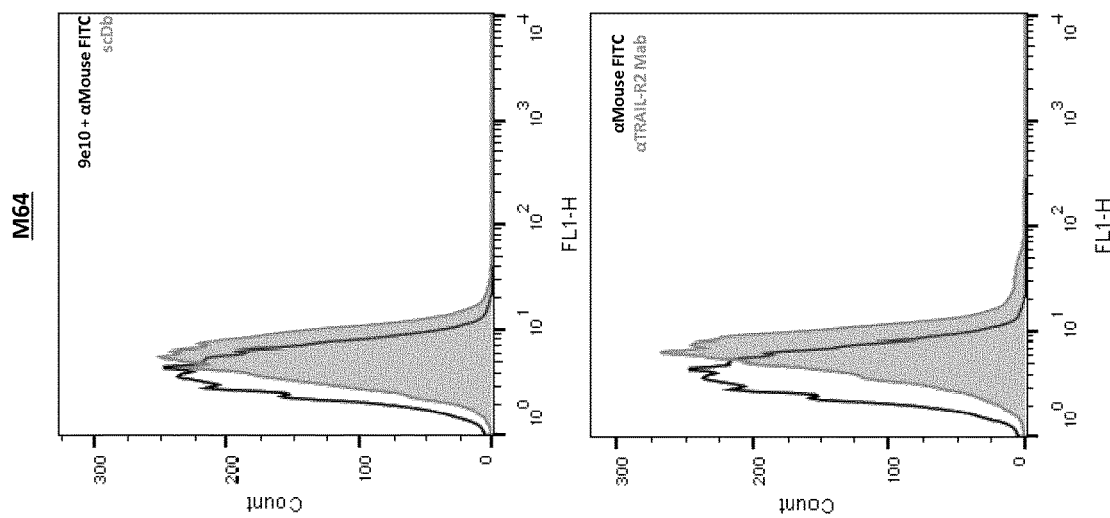
Figure 3:
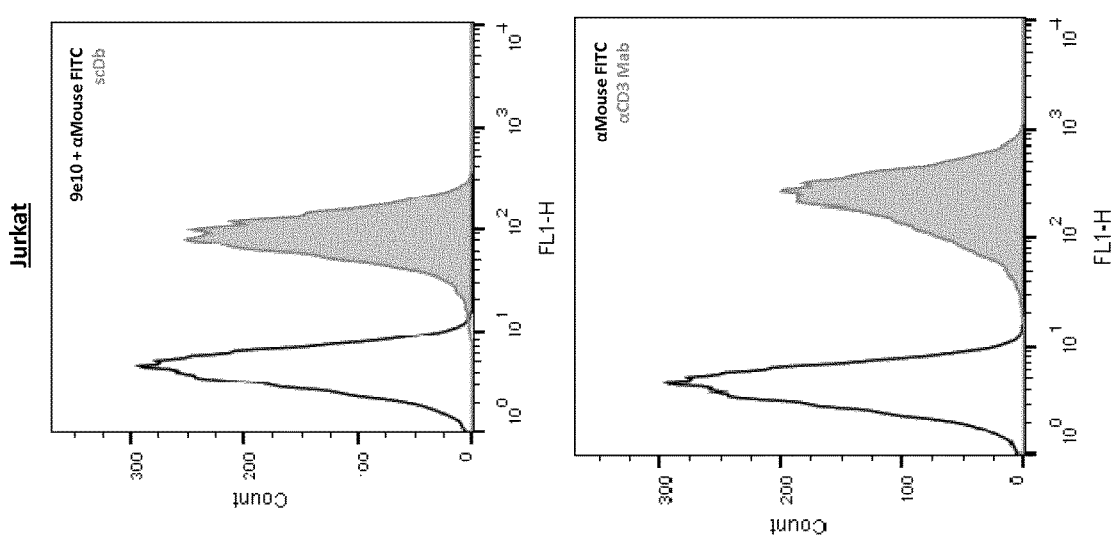
Figure 3A:
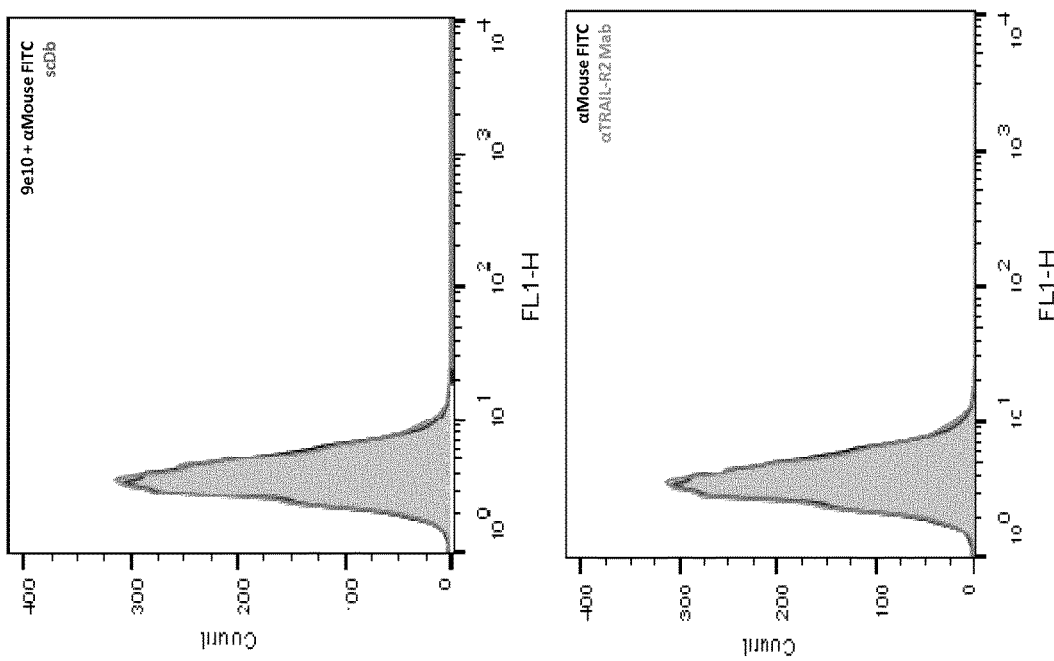
Figure 3:
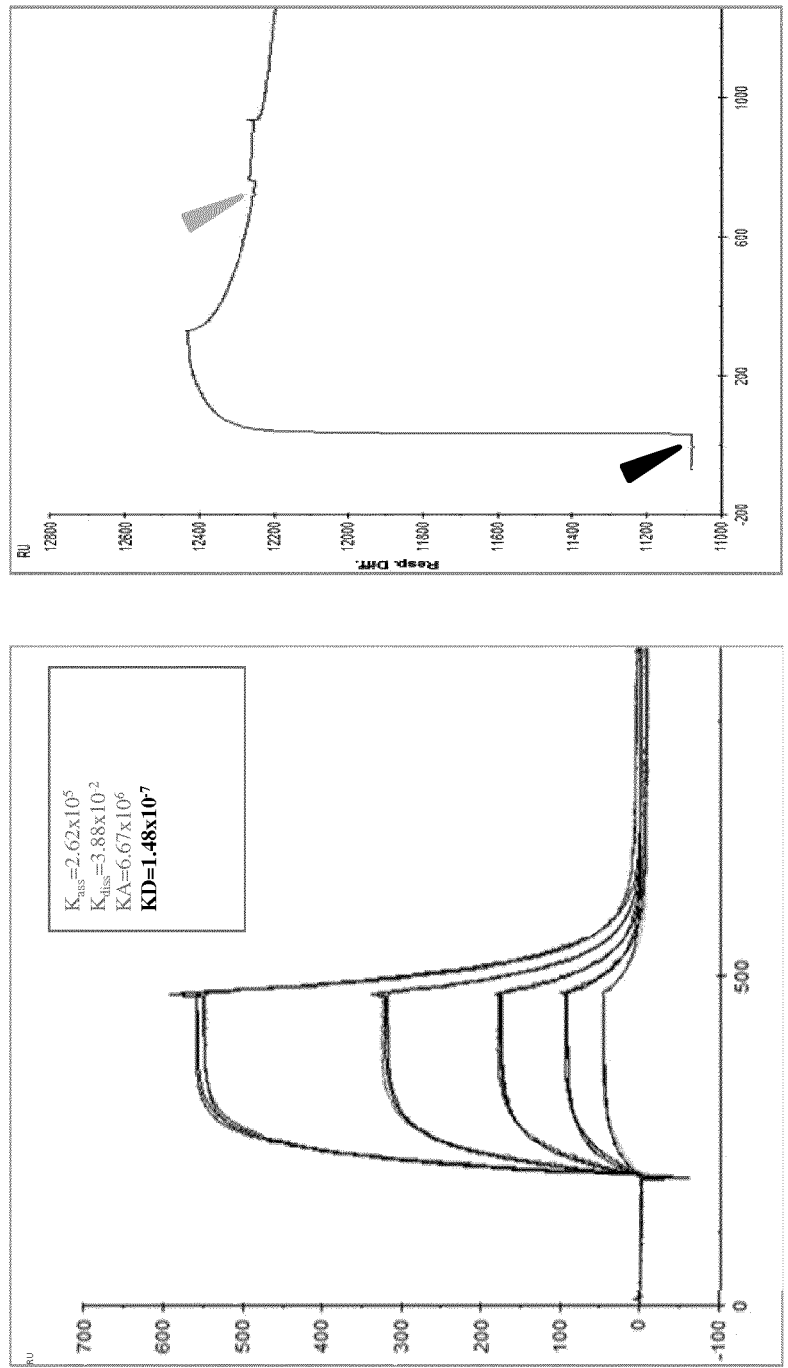
Figure 3:
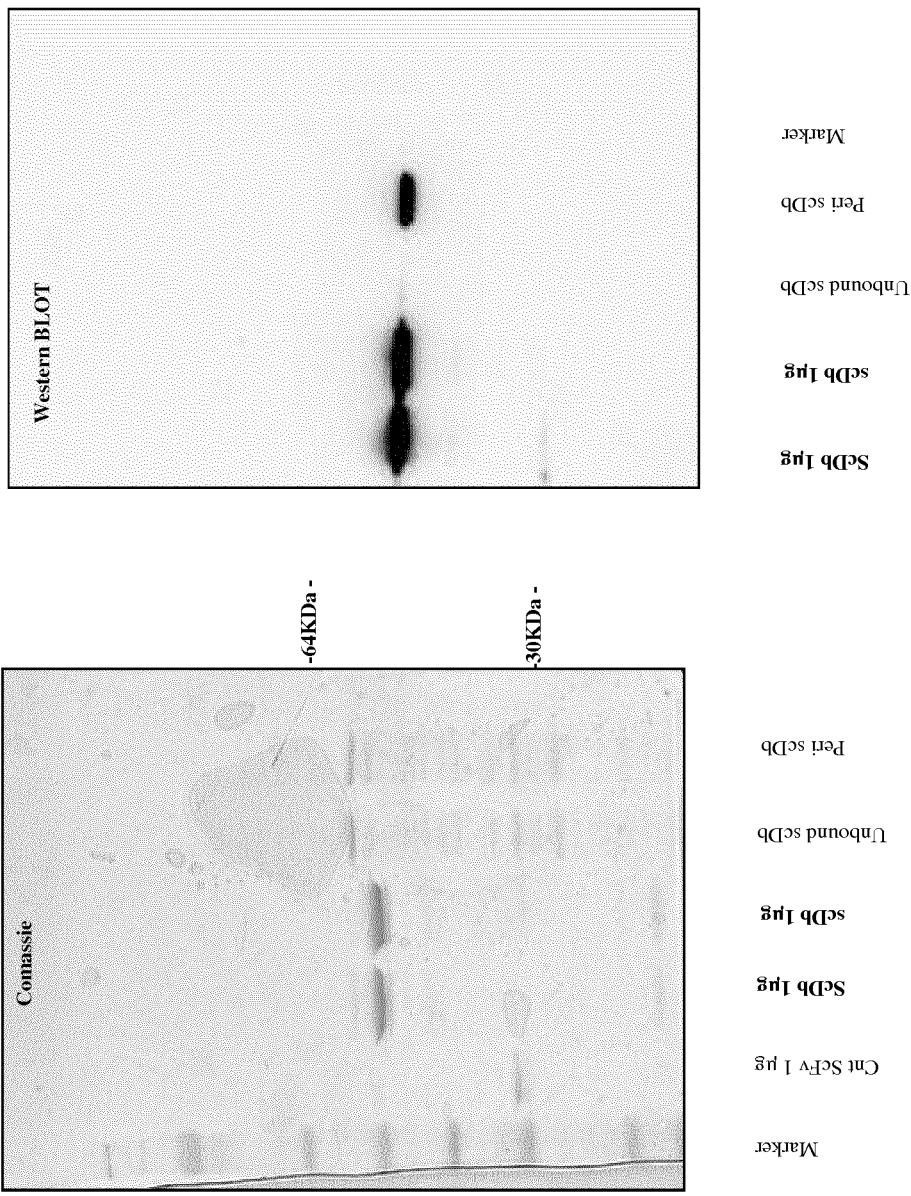
Figure 3:
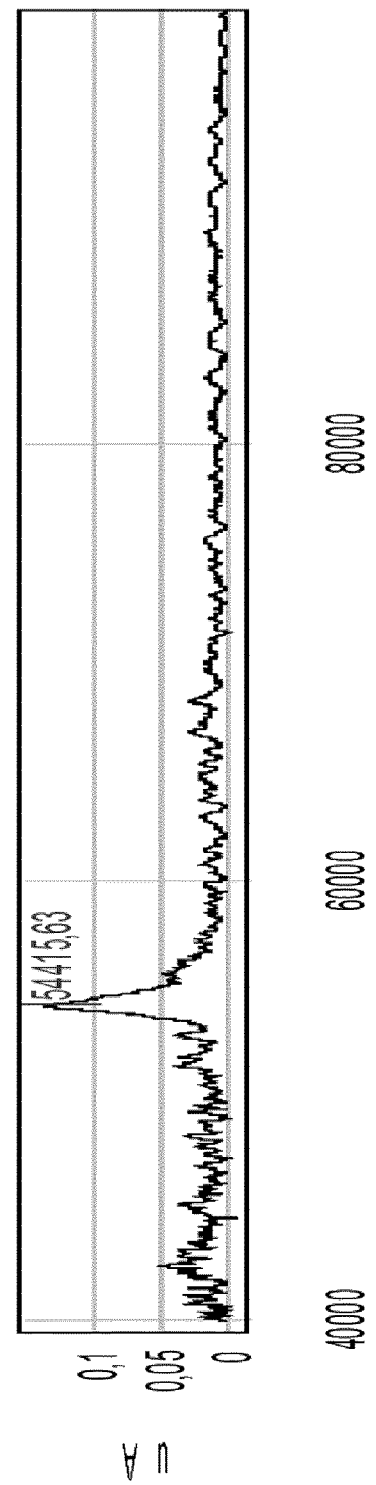

The purified scDb was tested by electrophoresis on 4-12% SDS gel and either stained with Comassie blue or, after blotting on a nitrocellulose membrane, using MAb anti-His specific to the exahystidinil epitope. The detected band was at the right molecular weight and no other bands were observed (FIG. 3C). Size exclusion chromatography, on a SUPEROSE 12 10/300 column, analysis showed that the purity of the scDb after purification is greater than 97%. FACScalibur tests demonstrated the specific binding of the scDb on TRAIL-R2+ melanoma cells and on CD3+ Jurkat cells. No binding was observed on MDA-MB-468 completely negative cells for both specificities (FIG. 3 A).

BIAcore Analysis.

The TRAIL-R2 binding affinity of the BsAb was measured by plasmon surface resonance using BIAcore. The analysis was performed using recombinant human TRAIL-R2 immobilized on the chip. Based on experimental data, association and dissociation-curves were calculated and kinetic evaluations gave rise to a calculated affinity constant (KD) of $1.48 \times 10^7$ nM (FIG. 3B, left panel).

To evaluate the binding competition of the scDb anti-TRAIL-arm with sTRAIL, the recombinant receptor was immobilized on a chip and was saturated with 1 µM of soluble TRAIL. Analysis showed strong competition for the same binding site because no BsAb binding on sTRAIL saturated TRAIL-R2 is observed (FIG. 3B right panel). For this reason we investigated if the scDb could act like sTRAIL in an agonistic manner.

ScDb Agonistic Activity.

To deeply characterize TRAILR2 agonistic activity, we used scDb in monomeric form or multimerized with different methods. The first method, that we used, exploited the possibility of recognition of the Myc tag exerted by 9E10 monoclonal antibody: this antibody could recognize myc tag and allow dimerization of the scDb and, if incubated with Fc-specific anti-mouse antibody, which could bind Fc of 9E10, could have an artificial tetrameric form of the scDb. The second method exploits the biotin tetramerization properties of streptavidin: scDb was biotinilated and incubated with streptavidin. Tetramerized scDbs were isolated with SEC and used to treat cells. M15, M64 and M41 are cells that have different TRAIL-R2 expression and sensitivity to sTRAIL treatment: in particular M15 are sTRAIL-sensitive and high-expression; M41 are sTRAIL partially sensitive and high expression while M64 are resistant with low expression. All the methods used to multimerize the scDb are suggestive of agonistic effect and in particular the scDb multimerized with Biotin-streptavidin strategy demonstrate the best agonistic activity Induction of Cytotoxicity by scDb The ability of the bispecific antibody to induce growth inhibition or cytotoxicity on tumor cells was investigated by redirecting activated or non activated PBLs, isolated from healthy donors, on tumor cells. M15, M41 and M64 melanoma cell lines, A2774, A2780, SKOV3, NL3507 and A431 ovarian cancer cell lines, A431 epidermoid cancer cell line, MDA-MB-231 and MT-3 triple negative breast carcinoma cell lines, LnCap, DU145 and PC3 prostate carcinoma cell lines, CaCO2 colorectal adenocarcinomas cell line, HepG2 hepatocellular carcinoma cell line and SkMes lung squamous carcinoma cell line expressing TRAIL-R2 were used as target cells. MDA-MB-468, TRAIL-R2 negative cell line, were used to test the absence of off-target cytotoxicity; HEK-293, normal kidney immortalized cell line, were used to exclude toxicity on normal cells. The effect of the scDb was measured using CellTiterGlo for growth inhibition or Calcein AM-release assay for direct T-cells cytotoxicity. First experiments were performed using different concentrations of BsAb (starting from 1 μg/ml with dilutions 1:2 until reaching 0.01 μg/ml), different effector to target ratios (20:1 to 1.25:1) and activated or non-activated PBLs.

Best results were obtained using a concentration of 0.5 μg/ml and E:T ratio of 5:1.

The scDb shows a good effect on all the used tumor cell lines. The data relative to M64 and M15 is reported in FIG. 4A.

Other experiments were performed using these conditions to test the reproducibility of the results using PBLs extracted from peripheral blood of 10 different healthy donors. To avoid distortions due to different cytotoxic power of PBMC derived from different donors, before the treatment of tumor cells, PBMC basal activation state was evaluated by FACS. If CD69 and CD25 markers are too high, PBMC were considered just activated and were not used in treatment. On melanoma cell lines, treatment with scDb and PBMC repeated the same results. No off-target cytotoxicity was observed in MDA-MB-468. Furthermore, the very low standard deviation calculated in each group indicated that the treatment is repeatable and is not influenced by the different PBLs pools (FIG. 4B).

In order to further characterize the reactivity of bispecific antibody, the presence of TRAIL-R2 receptor on different cancer cell lines was evaluated. Surface expression of TRAIL-R2 was analyzed by FACS using anti-TRAIL-R2 mAb. From this analysis we found that INT-Ov-11, A2774, A2780, SKOV3, NL3507 ovarian carcinoma cell lines, MDA-MB-231 and MT-3 triple negative breast carcinoma cell lines, LnCap, DU145 and PC3 prostate carcinoma cell lines, CaCO2 colorectal adenocarcinomas cell line, HepG2 hepatocellular carcinoma cell line, SkMes lung squamous carcinoma cell line, A431 epidermoid cancer cell line, expresses TRAIL-R2 and were used as target cells.

HEK-293, a normal kidney immortalized cell line, presented a great level of TRAIL-R2 and were used to exclude toxicity on normal cells.

After retargeting of PBLs (E:T ratio of 5:1) with 0.5 ug/ml of scDb we observed that the BsAb was capable of inducing target cell growth inhibition for all the cell lines used. No cytotoxicity was observed on treated HEK-293 (FIG. 4C-4D)

Calcein AM-Release

To investigate direct T-cell cytotoxicity, calcein AM (calcein-acetoxymethyl diacetylester) release was used (Lichtenfels et al., 1994 and Roden et al., 1999), a method that was comparable with $^{51}Cr$ release. Calcein-AM concentration for tumor target cell number and density were determined by incubating cells to a concentration range from 1-10 μM, evaluating the optimal separation between maximal and spontaneous release (data not shown). Treatment with scDb showed good results and was able to retarget T-cells to lyse melanoma cells M15, M64 and M41. Retarget T-cells could damage tumor cells and calcein was released in the medium. After 4 hours cytotoxicity was about 50% for TRAIL-R2 high expression M15 and M41 and about 30% for low expression M64. After 16 hours the cytotoxicity reached 100% for all treated cell lines. No direct cytotoxicity was observed in MDA-MB-468, TRAIL-R2 negative cell line (FIG. 4E).

T-Cell Activation

To dissect the mechanism of cytotoxicity, PBMC state of activation, after the co-incubation with TRAIL-R2 positive and negative tumor and normal cells, was analyzed. CD69 and CD25 activation markers, expressed on T-cell present in PBMC after incubation with TRAIL-R2+ cells, increased only in presence of scDb. By contrast, no up-regulation of the two markers was present in absence of the scDb or after co-culture with TRAIL-R2-MDA-MB-468 or with TRAIL-R2 high-expression HEK-293 normal cells (FIG. 6A). Experiments performed treating M15 cell line revealed that a dose-dependent expression of the T-cell activation markers CD25, CD137, CD69 and PD-1 was induced both in the $CD4^+$ and in the $CD8^+$ T-cells subpopulations (FIG. 6B).

T cell activation, after the scDb-mediated retargeting on tumor cells, was further demonstrated by the increase of the concentration of cytokines released in the medium. In particular FIG. 7 shows that an increase of production of these cytokines was specifically induced only in presence of scDb with a peak of production at 24 hours. Cytokines production, respect to 24 h supernatants, decreased after 48 h and returned similar after 72 h. At all the four times, measured cytokines in scDb treated media are higher respect to those produced in media of cells treated with only PBMC. No cytokines production was observed using negative TRAIL-R2 or normal cells.

Materials and Methods:
BIAcore

Binding of the BsAb anti-TRAIL-R2 arm was evaluated by surface plasmon resonance using a BIAcore 2000 equipped with research-grade CM5 sensor chips (Biacore AB, Uppsala, Sweden). Recombinant human TRAIL-R2 (R&D Systems) and BSA (Thermo Scientific) uncorrelated protein were immobilized on two different lanes of CM5 sensor chips using a standard amine-coupling protocol, with N-hydroxysuccinimide (NHS), 1-Ethyl-3-(3-dimethylaminopropyl)-carbodiimide (EDC) and Ethanolamine hydrochloride (pH 8.5). BsAb was injected for 3 min at 30 μL/min flow rate. Kinetic analyses were performed at concentrations ranging from 400 to 25 nM of scDb. The restoring of initial baseline was verified after each injection. The data obtained were analyzed by the BIAevaluation software 3.2 (global fitting) assuming a 1:1 Langmuir-binding model.

Biochemical Characterization and Integrity

The size and the homogeneity were analysed by sodium dodecyl sulphate-polyacrylamide gel electrophoresis (SDS-PAGE), western blotting and with mass spectrometry (SELDI-TOF).

Potential dimerization was analyzed by size exclusion chromatography on a SUPEROSE 12 10/300 (range separation: 300 Kd-10 Kd; GE Healthcare)

Isolation of PBLs.

PBMC were isolated from healthy donors' buffy coat by Ficoll density gradient centrifugation standard protocol (Ficoll plus hystopaque, GE Healthcare). Isolated PBMC were resuspended in RPMI 1640 complete medium and cell number was adjusted to $1\times10^6$/ml. The flask was lied down, for 30 minutes at 37° C. in a 5% $CO_2$ humidified incubator, to allow the monocytes attachment. PBLs present in the supernatant were removed and put in another flask. PBLs were cultured on RPMI1640 with 5% FBS or were activated using IL-2 and PHA for 4 days.

Tumor/Normal Cells Proliferation Inhibition and Cytotoxicity Assays

Redirected T-cell proliferation inhibition was evaluated by MTT assay using PBLs and a set of different TRAIL-R2$^+$ cell lines. $1.2\times10^4$ cells were plated in each well of a 96-well flat bottom plate with the appropriate medium and incubated ON to allow their attachment. 0.5 μg/ml of scDb was added and the cells were incubated for 1 hour before adding PBLs (E:T Ratio: 5:1). As negative controls: untreated cells, cells incubated only with scDb or cells incubated with only PBLs were used. After 48 or 96 hours, supernatant was removed and wells were washed three times with PBS to remove PBLs. In each well 100 μl of fresh medium containing 0.5 mg/ml of MTT salt were added. After 3 hours supernatant was discarded and 150 μl of MTT solvent (isopropanol+4 mM HCl+0.1% NP40) were used to resuspend formed formazan salts. Absorbance at 590 nm (620 nm reference filter) was read using a Biorad-550 microplate reader.

Redirected T-cell citotoxicity was assayed by the Calcein AM (Biovision Inc) release assay. $10^6$ target cells were resuspended in 1 ml of complete medium containing 15 μM of calcein-AM, incubated 30 minutes at 37° C. and washed 3 times with fresh medium. $10^4$ cells were seeded in 96-well round bottom plates following the same treatment (three triplicates for each) used for proliferation inhibition assay. 6 replicate wells were used for the measurement of spontaneous release and 6 for maximum release (target cells in medium containing 2% Triton X-100). After 4 hours, plates were centrifuged 1500 rpm for 10 minutes and supernatant, containing released fluorescent calcein, was transferred in black walled 96-well plate. Fluorescence intensity was measured by Ultra multiplate reader (Tecan Group, Mannedorf/Zurich, Switzerland), with extinction/emission wavelengths of 485/535 nm.

T Cell Activation

Activation Markers Evaluation

TRAIl-R2+ melanoma (M15, M41 and M64) and Hek-293 normal cells and TRAIl-R2-MDA-MB-468 cells were used as target cells and were grown in RPMI 1640 into 48-well plates (Corning) at a density of $3.5\times10^4$ cells for well. After 12 hours 0.5 ug/ml of scDb was added and incubated 1 h to allow the binding to TRAIL-R2 present on tumor cells. Freshly isolated human PBMC were used as effector cells and added to the scDb treated/untreated target cells at an effector-to-target ratio of 5:1. After incubation for 16 h at 37° C. in 5% CO2, T-cells contained in the supernatant were recovered, washed with PBS and stained with anti-human CD137 (Miltenyi Biotec), anti-human PD-1 BV421 (Biolegend), anti-human CD69 (BD Biosciences) and anti-human CD25 (Caltag Laboratories), labeled with different fluorochromes, for 30 min on ice. After washing three times with PBS+FCS 1%, the cells were analyzed by flow cytometry at FACSCalibur.

Determination of Cytokines Release (Bioplex)

To determine amounts of secreted IFN-γ, IL-4, TNF, and IL-2, supernatants were collected daily for 4 days after the start of the treatment of tumor cells with scDb plus T-cells. Supernatants were analyzed for cytokine secretion using Bio-plex ProTM Human Cytokine standard 27-Plex, Group I (BIORAD), according to the manufacturer's protocol. The absorption of the samples was measured, and the obtained values were used to calculate the concentration of the cytokines in the samples, according to the values obtained for the standard series provided by the manufacturer.

From the above description and the above-noted examples, the advantage attained by the product described and obtained according to the present invention are apparent.

The invention claimed is:

1. A single-chain bispecific diabody comprising:
   a. a variable domain of a heavy chain of an immunoglobulin (VH) with a first specificity (A), wherein said heavy chain ($VH_A$) variable domain has the amino acid sequence according to SEQ ID NO:1, wherein the first specificity (A) is directed against the TRAIL-R2 antigen;
   b. a variable domain of a light chain of an immunoglobulin (VL) with a second specificity (B), wherein said light chain ($VL_B$) variable domain has the amino acid sequence according to SEQ ID NO:3, wherein the second specificity (B) is directed against a T lymphocyte CD3;
   c. a variable domain of a heavy chain of an immunoglobulin (VH) with the specificity (B), wherein said heavy chain ($VH_B$) variable domain has the amino acid sequence according to SEQ ID NO:5; and
   d. a variable domain of a light chain of an immunoglobulin (VL) with the specificity (A), wherein said light chain ($VL_A$) variable domain has the amino acid sequence according to SEQ ID NO:7;
   wherein the VH and VL domains of the single-chain bispecific antibody are connected in the order $VH_A$-$VL_B$-$VH_B$-$VL_A$, wherein each VH and VL domain is connected with a peptide linker, wherein said peptide linker between the $VH_A$ and the $VL_B$ domains and between the $VH_B$ and the $VL_A$ domains consist of four Glycine amino acid residues and one Serine amino acid residue (GGGGS) as encoded by SEQ ID NO:22, and the peptide linker between the $VL_B$ and the $VH_B$ domains consists of three linker sequences consisting of four Glycine amino acid residues and one Serine amino acid residues each $(GGGGS)_3$ as set forth in SEQ ID NO:15.

2. The single-chain bispecific antibody according to claim 1, having the amino acid sequence according to SEQ ID NO: 13.

3. A composition comprising a single-chain bispecific antibody according to claim 1 and a labelling agent.

4. A composition comprising a single-chain bispecific antibody according to claim 2 and a labelling agent.

5. The composition according to claim 3, wherein said labelling agent is chosen from the group consisting of a radionuclide and fluorescent nanoparticles.

6. A pharmaceutical composition comprising a single-chain bispecific antibody according to claim 1 and a pharmaceutically acceptable carrier.

7. A pharmaceutical composition comprising a single-chain bispecific antibody according to claim 2 and a pharmaceutically acceptable carrier.

8. The pharmaceutical composition according to claim 6, wherein said composition is formulated for intramuscular, intravenous infusion, subcutaneous, or inhalation administration routes.

9. The composition according to claim 5, further comprising at least one further compound, which is able to enhance or reduce its efficacy.

10. The pharmaceutical composition according to claim 6, further comprising at least one further compound, which is able to enhance or reduce its efficacy.

11. A method for redirecting the cytotoxic action of a T-lymphocyte to a TRAIL-R2 positive tumor cell, comprising the step of contacting said tumor cell with the single-chain bispecific antibody according to claim 1.

12. A method for redirecting the cytotoxic action of a T-lymphocyte to a TRAIL-R2 positive tumor cell, comprising the step of contacting said tumor cell with the single-chain bispecific antibody according to claim 2.

13. A method for treating a TRAIL-R2 Positive tumor in a patient comprising the step of administering the single-chain bispecific antibody according to claim 1.

14. A method for treating a TRAIL-R2 Positive tumor in a patient comprising the step of administering the single-chain bispecific antibody according to claim 2.

15. The method according to claim 13, wherein said tumor is selected from the group consisting of melanoma, ovarian carcinoma, breast carcinoma, prostate carcinoma, colorectal adenocarcinomas, hepatocellular carcinoma and lung squamous carcinoma.

16. The method according to claim 13, wherein said treatment is of a patient which is resistant or intolerant to previous treatment with at least one antitumor agent or wherein the treatment with an antitumor agent should be avoided.

* * * * *

SEQUENCE LISTING

```
<160> NUMBER OF SEQ ID NOS: 22

<210> SEQ ID NO 1
<211> LENGTH: 121
<212> TYPE: PRT
<213> ORGANISM: Homo sapiens
<220> FEATURE:
<221> NAME/KEY: misc_feature
<223> OTHER INFORMATION: variable domain of a heavy chain of an
      immunoglobulin (VH): VHa of 16e2 (Class IGHV 3-20*01)
```

<400> SEQUENCE: 1

Glu Val Gln Leu Val Gln Ser Gly Gly Val Glu Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Ser Thr Gly Tyr Ala Asp Ser Val
    50                  55                  60

Lys Gly Arg Val Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Ile Leu Gly Ala Gly Arg Gly Trp Tyr Phe Asp Leu Trp Gly
            100                 105                 110

Lys Gly Thr Thr Val Thr Val Ser Ser
            115                 120

<210> SEQ ID NO 2
<211> LENGTH: 363
<212> TYPE: DNA
<213> ORGANISM: Homo sapiens
<220> FEATURE:
<221> NAME/KEY: misc_feature
<223> OTHER INFORMATION: variable domain of a heavy chain of an
      immunoglobulin (VH): VHa

<400> SEQUENCE: 2
gaggtacagc tggtgcaatc aggtggtggg gttgagagac ccggagggag tctccggttg    60
tcttgtgctg ccagcggctt tacgttcgat gattacggga tgtcgtgggt taggcaagct   120
ccaggcaagg gcctagaatg ggtatctggg ataaattgga acggcgggtc aacagggtat   180
gctgatagtg tgaaaggcag ggttactatt tccagggata atgccaaaaa ttcgctgtat   240
cttcagatga attcgctgcg agcggaggat actgcagtct actactgtgc taagatcctt   300
ggagcaggcc gtggatggta ttttgactta tgggggaagg gtaccaccgt gacggtctcg   360
tct                                                                 363

<210> SEQ ID NO 3
<211> LENGTH: 108
<212> TYPE: PRT
<213> ORGANISM: Artificial
<220> FEATURE:
<223> OTHER INFORMATION: variable domain of a light chain of an
      immunoglobulin (VL): VLb (UCTH1)Humanized antibody with murine CDR

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

```
Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Arg
            100                 105
```

<210> SEQ ID NO 4
<211> LENGTH: 324
<212> TYPE: DNA
<213> ORGANISM: Artificial
<220> FEATURE:
<223> OTHER INFORMATION: amino acid sequence of a variable domain of a
      light chain of an immunoglobulin (VL): VLb (UCTH1) Humanized
      antibody with murine CDR

<400> SEQUENCE: 4

```
gatattcaaa tgactcagtc cccatcctca ctctcggcat cagttggtga tcgagtgacg      60
ataacatgta gggcctcgca ggacatccgc aactatctta actggtacca acaaaaacca     120
gggaaggctc aaaattact aatctattac acctcacgtc tcgaatcagg tgttcctagt     180
cgcttcagcg gatcaggttc cggaacagat tataccctta ctatatcgtc cctccaacca     240
gaagactttg ccacttatta ctgtcaacag ggcaacacct taccctggac ttttggacag     300
gggacaaaag tcgagattaa gcgc                                            324
```

<210> SEQ ID NO 5
<211> LENGTH: 122
<212> TYPE: PRT
<213> ORGANISM: Artificial
<220> FEATURE:
<223> OTHER INFORMATION: variable domain of a heavy chain of an
      immunoglobulin (VH): VHb (UCTH1) Humanized antibody with murine
      CDR

<400> SEQUENCE: 5

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Phe Thr Gly Tyr
            20                  25                  30

Thr Met Asn Trp Val Arg Gln Ala Pro Gly Lys Gly Leu Glu Trp Val
        35                  40                  45

Ala Leu Ile Asn Pro Tyr Lys Gly Val Ser Thr Tyr Asn Gln Lys Phe
    50                  55                  60

Lys Asp Arg Phe Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Tyr Gly Asp Ser Asp Trp Tyr Phe Asp Val Trp
            100                 105                 110

Gly Gln Gly Thr Leu Val Thr Val Ser Ser
        115                 120
```

<210> SEQ ID NO 6
<211> LENGTH: 366
<212> TYPE: DNA
<213> ORGANISM: Homo sapiens
<220> FEATURE:
<221> NAME/KEY: misc_feature
<223> OTHER INFORMATION: variable domain of a heavy chain of an
      immunoglobulin (VH): VHb

<400> SEQUENCE: 6

```
gaagtacaac tggttgagag tgggggcggt ttagttcaac cgggcggaag cctgagactt    60
tcgtgcgccg cgagtggata ttcttttacg ggctacacaa tgaactgggt ccggcaggca   120
ccaggaaagg ggcttgaatg ggtcgcttta ataaacccat ataagggcgt aagcacctat   180
aaccagaaat ttaagatcg tttcacaata tcagtcgata aatctaagaa taccgcctat    240
ctccaaatga attccctcag agctgaagat accgccgtgt attactgtgc aaggagcggt   300
tactatggcg attcagattg gtacttcgat gtgtgggac aggggacgct tgtaactgtg    360
tcgtcc                                                              366
```

<210> SEQ ID NO 7
<211> LENGTH: 107
<212> TYPE: PRT
<213> ORGANISM: Homo sapiens
<220> FEATURE:
<221> NAME/KEY: misc_feature
<223> OTHER INFORMATION: variable domain of a light chain of an immunoglobulin (VL): VLa of 16e2 (Class IGLV3-19*01)

<400> SEQUENCE: 7

```
Ser Glu Leu Thr Gln Asp Pro Ala Val Ser Val Ala Leu Gly Gln Thr
  1               5                  10                  15
Val Arg Ile Thr Cys Gln Gly Asp Ser Leu Arg Ser Tyr Tyr Ala Ser
                 20                  25                  30
Trp Tyr Gln Gln Lys Pro Gly Gln Ala Pro Val Leu Val Ile Tyr Gly
             35                  40                  45
Lys Asn Asn Arg Pro Ser Gly Ile Pro Asp Arg Phe Ser Gly Ser Ser
         50                  55                  60
Ser Gly Asn Thr Ala Ser Leu Thr Ile Thr Gly Ala Gln Ala Glu Asp
 65                  70                  75                  80
Glu Ala Asp Tyr Tyr Cys Asn Ser Arg Asp Ser Ser Gly Asn His Val
                 85                  90                  95
Val Phe Gly Gly Gly Thr Lys Leu Thr Val Leu
            100                 105
```

<210> SEQ ID NO 8
<211> LENGTH: 321
<212> TYPE: DNA
<213> ORGANISM: Homo sapiens
<220> FEATURE:
<221> NAME/KEY: misc_feature
<223> OTHER INFORMATION: variable domain of a light chain of an immunoglobulin (VL): VLa of 16e2 (Class IGLV3-19*01)

<400> SEQUENCE: 8

```
agtgaactaa ctcaggaccc cgctgtgtct gtcgcgcttg gccaaacggt gcggataacc    60
tgtcaaggtg acagtctaag gtcctattat gcatcttggt atcaacagaa acccggacaa   120
gcaccggttc tggttatcta cggtaaaaac aatcgcccct cgggtatacc tgatcgcttc   180
tccgggtcga gctccgggaa tacagcctct ctaacgataa cgggggctca agcagaagat   240
gaagcagact attattgcaa ttcaagggac agctctggca accacgtcgt ctttggggga   300
ggcacaaagt tgacagtcct t                                             321
```

<210> SEQ ID NO 9
<211> LENGTH: 21
<212> TYPE: DNA
<213> ORGANISM: Homo sapiens

```
<220> FEATURE:
<221> NAME/KEY: misc_feature
<223> OTHER INFORMATION: (sequence which comes before VHA domain, Sfi I
      restriction site)

<400> SEQUENCE: 9
gcggcccagc cggccatggc c                                              21

<210> SEQ ID NO 10
<211> LENGTH: 18
<212> TYPE: DNA
<213> ORGANISM: Homo sapiens
<220> FEATURE:
<221> NAME/KEY: misc_feature
<223> OTHER INFORMATION: (linker between VHA and VLB domains, Age I
      restriction site)

<400> SEQUENCE: 10
accggtggag gcggttca                                                  18

<210> SEQ ID NO 11
<211> LENGTH: 45
<212> TYPE: DNA
<213> ORGANISM: Homo sapiens
<220> FEATURE:
<221> NAME/KEY: misc_feature
<223> OTHER INFORMATION: (linker between VLB and VHB domains)

<400> SEQUENCE: 11
ggtggaggcg gttcaggcgg aggtggctct ggcggtggcg gatcg                    45

<210> SEQ ID NO 12
<211> LENGTH: 18
<212> TYPE: DNA
<213> ORGANISM: Homo sapiens
<220> FEATURE:
<221> NAME/KEY: misc_feature
<223> OTHER INFORMATION: (linker between VHB and VLA domains, Xba I
      restriction site)

<400> SEQUENCE: 12
ggtggaggcg gttctaga                                                  18

<210> SEQ ID NO 13
<211> LENGTH: 487
<212> TYPE: PRT
<213> ORGANISM: Homo sapiens
<220> FEATURE:
<221> NAME/KEY: misc_feature
<223> OTHER INFORMATION: single-chain bispecific antibody

<400> SEQUENCE: 13

Glu Val Gln Leu Val Gln Ser Gly Gly Gly Val Glu Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Val Thr Ile Ser Arg Asp Asn Ala Lys Asn Ser Leu Tyr
65                  70                  75                  80
```

```
Leu Gln Met Asn Ser Leu Arg Ala Glu Asp Thr Ala Val Tyr Tyr Cys
                85                  90                  95

Ala Lys Ile Leu Gly Ala Gly Arg Gly Trp Tyr Phe Asp Leu Trp Gly
            100                 105                 110

Lys Gly Thr Thr Val Thr Val Ser Ser Thr Gly Gly Gly Gly Ser Asp
            115                 120                 125

Ile Gln Met Thr Gln Ser Pro Ser Ser Leu Ser Ala Ser Val Gly Asp
            130                 135                 140

Arg Val Thr Ile Thr Cys Arg Ala Ser Gln Asp Ile Arg Asn Tyr Leu
145                 150                 155                 160

Asn Trp Tyr Gln Gln Lys Pro Gly Lys Ala Pro Lys Leu Leu Ile Tyr
                165                 170                 175

Tyr Thr Ser Arg Leu Glu Ser Gly Val Pro Ser Arg Phe Ser Gly Ser
            180                 185                 190

Gly Ser Gly Thr Asp Tyr Thr Leu Thr Ile Ser Ser Leu Gln Pro Glu
            195                 200                 205

Asp Phe Ala Thr Tyr Tyr Cys Gln Gln Gly Asn Thr Leu Pro Trp Thr
            210                 215                 220

Phe Gly Gln Gly Thr Lys Val Glu Ile Lys Arg Gly Gly Gly Gly Ser
225                 230                 235                 240

Gly Gly Gly Gly Ser Gly Gly Gly Ser Glu Val Gln Leu Val Glu
            245                 250                 255

Ser Gly Gly Gly Leu Val Gln Pro Gly Gly Ser Leu Arg Leu Ser Cys
            260                 265                 270

Ala Ala Ser Gly Tyr Ser Phe Thr Gly Tyr Thr Met Asn Trp Val Arg
            275                 280                 285

Gln Ala Pro Gly Lys Gly Leu Glu Trp Val Ala Leu Ile Asn Pro Tyr
            290                 295                 300

Lys Gly Val Ser Thr Tyr Asn Gln Lys Phe Lys Asp Arg Phe Thr Ile
305                 310                 315                 320

Ser Val Asp Lys Ser Lys Asn Thr Ala Tyr Leu Gln Met Asn Ser Leu
            325                 330                 335

Arg Ala Glu Asp Thr Ala Val Tyr Tyr Cys Ala Arg Ser Gly Tyr Tyr
            340                 345                 350

Gly Asp Ser Asp Trp Tyr Phe Asp Val Trp Gly Gln Gly Thr Leu Val
            355                 360                 365

Thr Val Ser Ser Gly Gly Gly Gly Ser Arg Ser Glu Leu Thr Gln Asp
            370                 375                 380

Pro Ala Val Ser Val Ala Leu Gly Gln Thr Val Arg Ile Thr Cys Gln
385                 390                 395                 400

Gly Asp Ser Leu Arg Ser Tyr Tyr Ala Ser Trp Tyr Gln Gln Lys Pro
            405                 410                 415

Gly Gln Ala Pro Val Leu Val Ile Tyr Gly Lys Asn Asn Arg Pro Ser
            420                 425                 430

Gly Ile Pro Asp Arg Phe Ser Gly Ser Ser Ser Gly Asn Thr Ala Ser
            435                 440                 445

Leu Thr Ile Thr Gly Ala Gln Ala Glu Asp Glu Ala Asp Tyr Tyr Cys
            450                 455                 460

Asn Ser Arg Asp Ser Ser Gly Asn His Val Val Phe Gly Gly Gly Thr
465                 470                 475                 480

Lys Leu Thr Val Leu Ala Ala
            485
```

<210> SEQ ID NO 14
<211> LENGTH: 1484
<212> TYPE: DNA
<213> ORGANISM: Homo sapiens
<220> FEATURE:
<221> NAME/KEY: misc_feature
<223> OTHER INFORMATION: single-chain bispecific antibody with vector
      term. upstream

<400> SEQUENCE: 14

```
gcggcccagc cggccatggc cgaggtacag ctggtgcaat caggtggtgg ggttgagaga      60
cccggaggga gtctccggtt gtcttgtgct gccagcggct ttacgttcga tgattacggg     120
atgtcgtggg ttaggcaagc tccaggcaag ggcctagaat gggtatctgg ataaaattgg     180
aacggcgggt caacagggta tgctgatagt gtgaaaggca gggttactat ttccagggat     240
aatgccaaaa attcgctgta tcttcagatg aattcgctgc gagcggagga tactgcagtc     300
tactactgtg ctaagatcct tggagcaggc cgtggatggt attttgactt atgggggaag     360
ggtaccaccg tgacggtctc gtctaccggt ggaggcggtt cagatattca atgactcag      420
tccccatcct cactctcggc atcagttggt gatcgagtga cgataacatg tagggcctcg     480
caggacatcc gcaactatct taactggtac aacaaaaac cagggaaggc tccaaaatta     540
ctaatctatt acacctcacg tctcgaatca ggtgttccta gtcgcttcag cggatcaggt     600
tccggaacag attataccct tactatatcg tccctccaac cagaagactt tgccacttat     660
tactgtcaac agggcaacac cttaccctgg acttttggac aggggacaaa agtcgagatt     720
aagcgcggtg gaggcggttc aggcggaggt ggctctggcg gtggcggatc ggaagtacaa     780
ctggttgaga gtgggggcgg tttagttcaa ccggcggaa gcctgagact tcgtgcgcc      840
gcgagtggat attctttac gggctacaca atgaactggg tccggcaggc accaggaaag     900
gggcttgaat gggtcgcttt aataaaccca tataagggcg taagcaccta accagaaa      960
tttaaagatc gtttcacaat atcagtcgat aaatctaaga ataccgccta tctccaaatg    1020
aattccctca gagctgaaga taccgccgtg tattactgtg caaggagcgg ttactatggc    1080
gattcagatt ggtacttcga tgtgtgggga caggggacgc ttgtaactgt gtcgtccggt    1140
ggaggcggtt ctagaagtga actaactcag gaccccgctg tgtctgtcgc gcttggccaa    1200
acggtgcgga taacctgtca aggtgacagt ctaaggtcct attatgcatc ttggtatcaa    1260
cagaaacccg gacaagcacc tgttctggtt atctacggta aaaacaatcg cccttcgggt    1320
atacctgatc gcttctccgg gtcgagctcc gggaatacag cctctctaac gataacgggg    1380
gctcaagcag aagatgaagc agactattat tgcaattcaa gggacagctc tggcaaccac    1440
gtcgtctttg ggggaggcac aaagttgaca gtccttgcgg ccgc                    1484
```

<210> SEQ ID NO 15
<211> LENGTH: 15
<212> TYPE: PRT
<213> ORGANISM: Homo sapiens
<220> FEATURE:
<221> NAME/KEY: misc_feature
<223> OTHER INFORMATION: (alternative linker between VLB and VHB
      domains)

<400> SEQUENCE: 15

```
Gly Gly Gly Gly Ser Gly Gly Gly Gly Ser Gly Gly Gly Gly Ser
1               5                   10                  15
```

-continued

```
<210> SEQ ID NO 16
<211> LENGTH: 511
<212> TYPE: PRT
<213> ORGANISM: Homo sapiens
<220> FEATURE:
<221> NAME/KEY: misc_feature
<223> OTHER INFORMATION: single-chain bispecific antibody with His and
      Myc tags

<400> SEQUENCE: 16
```

Glu Val Gln Leu Val Gln Ser Gly Gly Gly Val Glu Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Ser Thr Gly Tyr Ala Asp Ser Val
    50                  55                  60

Lys Gly Arg Val Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Ile Leu Gly Ala Gly Arg Gly Trp Tyr Phe Asp Leu Trp Gly
            100                 105                 110

Lys Gly Thr Thr Val Thr Val Ser Ser Thr Gly Gly Gly Ser Asp
        115                 120                 125

Ile Gln Met Thr Gln Ser Pro Ser Ser Leu Ser Ala Ser Val Gly Asp
    130                 135                 140

Arg Val Thr Ile Thr Cys Arg Ala Ser Gln Asp Ile Arg Asn Tyr Leu
145                 150                 155                 160

Asn Trp Tyr Gln Gln Lys Pro Gly Lys Ala Pro Lys Leu Leu Ile Tyr
                165                 170                 175

Tyr Thr Ser Arg Leu Glu Ser Gly Val Pro Ser Arg Phe Ser Gly Ser
            180                 185                 190

Gly Ser Gly Thr Asp Tyr Thr Leu Thr Ile Ser Ser Leu Gln Pro Glu
        195                 200                 205

Asp Phe Ala Thr Tyr Tyr Cys Gln Gln Gly Asn Thr Leu Pro Trp Thr
    210                 215                 220

Phe Gly Gln Gly Thr Lys Val Glu Ile Lys Arg Gly Gly Gly Ser
225                 230                 235                 240

Gly Gly Gly Gly Ser Gly Gly Gly Ser Glu Val Gln Leu Val Glu
                245                 250                 255

Ser Gly Gly Gly Leu Val Gln Pro Gly Gly Ser Leu Arg Leu Ser Cys
            260                 265                 270

Ala Ala Ser Gly Tyr Ser Phe Thr Gly Tyr Thr Met Asn Trp Val Arg
            275                 280                 285

Gln Ala Pro Gly Lys Gly Leu Glu Trp Val Ala Leu Ile Asn Pro Tyr
            290                 295                 300

Lys Gly Val Ser Thr Tyr Asn Gln Lys Phe Lys Asp Arg Phe Thr Ile
305                 310                 315                 320

Ser Val Asp Lys Ser Lys Asn Thr Ala Tyr Leu Gln Met Asn Ser Leu
                325                 330                 335

Arg Ala Glu Asp Thr Ala Val Tyr Tyr Cys Ala Arg Ser Gly Tyr Tyr
            340                 345                 350

Gly Asp Ser Asp Trp Tyr Phe Asp Val Trp Gly Gln Gly Thr Leu Val
        355                 360                 365

```
Thr Val Ser Ser Gly Gly Gly Ser Arg Ser Glu Leu Thr Gln Asp
    370             375                 380

Pro Ala Val Ser Val Ala Leu Gly Gln Thr Val Arg Ile Thr Cys Gln
385                 390                 395                 400

Gly Asp Ser Leu Arg Ser Tyr Tyr Ala Ser Trp Tyr Gln Gln Lys Pro
                405                 410                 415

Gly Gln Ala Pro Val Leu Val Ile Tyr Gly Lys Asn Asn Arg Pro Ser
            420                 425                 430

Gly Ile Pro Asp Arg Phe Ser Gly Ser Ser Ser Gly Asn Thr Ala Ser
            435                 440                 445

Leu Thr Ile Thr Gly Ala Gln Ala Glu Asp Glu Ala Asp Tyr Tyr Cys
    450                 455                 460

Asn Ser Arg Asp Ser Ser Gly Asn His Val Val Phe Gly Gly Gly Thr
465                 470                 475                 480

Lys Leu Thr Val Leu Ala Ala Ala His His His His His His Gly Ala
                485                 490                 495

Ala Glu Gln Lys Leu Ile Ser Glu Glu Asp Leu Asn Gly Ala Ala
                500                 505                 510

<210> SEQ ID NO 17
<211> LENGTH: 254
<212> TYPE: PRT
<213> ORGANISM: Homo sapiens
<220> FEATURE:
<221> NAME/KEY: misc_feature
<223> OTHER INFORMATION: Clone 7 anti-TRAIL-R2 ScFv isolated with Phage
      Display (VH-LINKER-VL)

<400> SEQUENCE: 17

Gln Val Gln Leu Val Gln Ser Gly Ala Glu Val Lys Ser Pro Gly Glu
1               5                   10                  15

Ser Leu Lys Ile Ser Cys Lys Gly Leu Gly Tyr Asp Phe Thr Thr Tyr
                20                  25                  30

Trp Ile Ala Leu Val Arg Gln Met Pro Gly Lys Gly Leu Glu Tyr Met
            35                  40                  45

Gly Leu Ile Tyr Pro Gly Asp Ser Asp Thr Lys Tyr Ser Pro Ser Phe
50                  55                  60

Gln Gly Gln Val Thr Ile Ser Val Asp Lys Ser Val Ser Thr Ala Tyr
65                  70                  75                  80

Leu Gln Trp Ser Ser Leu Arg Pro Ser Asp Ser Ala Val Tyr Phe Cys
                85                  90                  95

Ala Arg His Asp Val Gly Tyr Cys Ser Ser Ser Asn Cys Ala Lys Arg
            100                 105                 110

Pro Glu Tyr Phe Gln His Trp Gly Gln Gly Thr Leu Val Thr Val Ser
        115                 120                 125

Ser Gly Gly Gly Gly Ser Gly Gly Gly Gly Ser Gly Gly Gly Gly Ser
    130                 135                 140

Asp Ile Val Met Thr Gln Ser Pro Ser Phe Leu Ser Ala Ser Val Gly
145                 150                 155                 160

Asp Arg Ile Thr Ile Thr Cys Arg Ala Ser His Gly Ile Ser Ser Tyr
                165                 170                 175

Leu Ala Trp Tyr Gln Gln Lys Pro Gly Lys Ala Pro Lys Leu Leu Ile
            180                 185                 190

Tyr Ala Ala Ser Thr Leu Gln Ser Gly Val Pro Ser Arg Phe Gly Gly
        195                 200                 205
```

```
Ser Gly Ser Gly Thr Glu Phe Thr Leu Thr Val Ser Gly Leu Gln Pro
    210                 215                 220

Glu Asp Phe Ala Thr Tyr Tyr Cys Gln His Leu Asn Ser Tyr Pro Leu
225                 230                 235                 240

Thr Phe Gly Gly Gly Thr Lys Leu Glu Ile Lys Arg Ala Ala
                245                 250

<210> SEQ ID NO 18
<211> LENGTH: 242
<212> TYPE: PRT
<213> ORGANISM: Homo sapiens
<220> FEATURE:
<221> NAME/KEY: misc_feature
<223> OTHER INFORMATION: Clone 8 anti-TRAIL-R2 ScFv isolated with Phage
      Display (VH-LINKER-VL)

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gln Gln Gly Gln Val Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Trp Asn Arg Phe Asp Tyr Trp Gly Gln Gly Thr Leu Val
            100                 105                 110

Ile Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Ala Ala Ser Gly Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln His Ser
    210                 215                 220

Met Ser Pro Asn Thr Phe Gly Gln Gly Thr Lys Val Glu Ile Lys Arg
225                 230                 235                 240

Ala Ala

<210> SEQ ID NO 19
<211> LENGTH: 250
<212> TYPE: PRT
<213> ORGANISM: Homo sapiens
<220> FEATURE:
<221> NAME/KEY: misc_feature
<223> OTHER INFORMATION: Clone 44 anti-TRAIL-R2 ScFv isolated with Phage
      Display (VH-LINKER-VL)
```

<400> SEQUENCE: 19

```
Gln Val His Leu Arg Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Ser Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ser Glu Asp Thr Ala Val Tyr Tyr Cys
                85                  90                  95

Ala Arg Asp Pro Asn His Gly Gly Asp Arg Arg Asp Asp Ala Leu Asp
            100                 105                 110

Met Trp Gly Gln Gly Thr Met Val Thr Val Ser Ser Gly Gly Gly Gly
        115                 120                 125

Ser Gly Gly Gly Gly Ser Gly Gly Gly Ser Ser Glu Leu Thr Gln
    130                 135                 140

Asp Pro Ala Val Ser Val Ala Leu Gly Gln Thr Val Arg Ile Thr Cys
145                 150                 155                 160

Gln Gly His Ser Leu Arg Ser Tyr Phe Ala Ser Trp Tyr Gln Gln Arg
                165                 170                 175

Pro Arg Gln Ala Pro Thr Leu Val Ile Tyr Gly Lys Asn Asn Arg Pro
            180                 185                 190

Ser Gly Ile Pro Asp Arg Phe Ser Gly Ser Ser Ser Gly Asn Thr Ala
        195                 200                 205

Ser Leu Thr Ile Thr Gly Ala Gln Ala Glu Asp Glu Ala Asp Tyr Tyr
    210                 215                 220

Cys Gly Ser Arg Asp Ser Ser Thr His Arg Gly Val Phe Gly Gly
225                 230                 235                 240

Gly Thr Lys Leu Thr Val Leu Gly Ala Ala
                245                 250
```

<210> SEQ ID NO 20
<211> LENGTH: 231
<212> TYPE: PRT
<213> ORGANISM: Homo sapiens
<220> FEATURE:
<221> NAME/KEY: misc_feature
<223> OTHER INFORMATION: Clone 56 anti-TRAIL-R2 ScFv isolated with Phage
      Display (VH-LINKER-VL)

<400> SEQUENCE: 20

```
Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ala Asn Gly Lys Met Thr Gln Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95
```

```
Lys Arg Trp Asn Arg Phe Asp Tyr Trp Gly Gln Gly Thr Leu Val Ile
                100                 105                 110

Val Ser Ser Gly Gly Gly Gly Ser Gly Gly Gly Ser Gly Gly Gly
            115                 120                 125

Gly Ser Asp Ile Gln Leu Thr Gln Ser Pro Ala Ile Met Ser Ala Ser
        130                 135                 140

Pro Gly Glu Lys Val Thr Met Thr Cys Arg Ala Ser Ser Ser Val Ser
145                 150                 155                 160

Tyr Met Asn Trp Tyr Gln Gln Lys Ser Gly Thr Ser Pro Lys Arg Trp
                165                 170                 175

Ile Tyr Asp Thr Ser Lys Val Ala Ser Gly Val Pro Tyr Arg Phe Ser
            180                 185                 190

Gly Ser Gly Ser Gly Thr Ser Tyr Ser Leu Thr Ile Ser Ser Met Glu
        195                 200                 205

Ala Glu Asp Ala Ala Thr Tyr Tyr Cys Gln Gln Trp Ser Ser Gly Gln
210                 215                 220

Gly Thr Lys Leu Glu Ile Lys
225                 230

<210> SEQ ID NO 21
<211> LENGTH: 1463
<212> TYPE: DNA
<213> ORGANISM: Homo sapiens
<220> FEATURE:
<221> NAME/KEY: misc_feature
<223> OTHER INFORMATION: single-chain bispecific antibody

<400> SEQUENCE: 21
gaggtacagc tggtgcaatc aggtggtggg gttgagagac ccggagggag tctccggttg     60
tcttgtgctg ccagcggctt tacgttcgat gattacggga tgtcgtgggt taggcaagct    120
ccaggcaagg gcctagaatg gtatctgggg ataaaattgga acggcgggtc aacagggtat    180
gctgatagtg tgaaaggcag ggttactatt tccaggtata atgccaaaaa ttcgctgtat    240
cttcagatga attcgctgcg agcggaggat actgcagtct actactgtgc taagatcctt    300
ggagcaggcc gtggatggta ttttgactta tggggaaagg gtaccaccgt gacggtctcg    360
tctaccggtg gaggcggttc agatattcaa atgactcagt ccccatcctc actctcggca    420
tcagttggtg atcgagtgac gataacatgt agggcctcgc aggacatccg caactatctt    480
aactggtacc aacaaaaacc agggaaggct ccaaaattac taatctatta caccctcacgt    540 ctcgaatcag gtgttcctag tcgcttcagc ggatcaggtt ccggaacaga ttataccctt    600
actatatcgt ccctccaacc agaagacttt gccacttatt actgtcaaca gggcaacacc    660
ttaccctgga cttttggaca ggggacaaaa gtcgagatta gcgcggtgg aggcggttca    720 ggcggaggtg gctctggcgg tggcggatcg gaagtacaac tggttgagag tgggggcggt    780
ttagttcaac cggcggaag cctgagactt cgtgcgccg cgagtggata ttcttttacg    840
ggctacacaa tgaactgggt ccggcaggca ccaggaaagg gcttgaatg gtcgctttta    900 ataaacccat ataagggcgt aagcacctat aaccagaaat ttaagatcg tttcacaata    960 tcagtcgata aatctaagaa taccgcctat ctccaaatga attccctcag agctgaagat    1020
accgccgtgt attactgtgc aaggagcggt tactatggcg attcagattg gtacttcgat    1080
gtgtggggac aggggacgct tgtaactgtg tcgtccggtg gaggcggttc tagaagtgaa    1140
ctaactcagg accccgctgt gtctgtcgcg cttggccaaa cggtgcggat aacctgtcaa    1200
ggtgacagtc taaggtccta ttatgcatct tggtatcaac agaaacccgg acaagcacct    1260
```

```
gttctggtta tctacggtaa aaacaatcgc ccttcgggta tacctgatcg cttctccggg    1320
tcgagctccg ggaatacagc ctctctaacg ataacggggg ctcaagcaga agatgaagca    1380
gactattatt gcaattcaag ggacagctct ggcaaccacg tcgtctttgg gggaggcaca    1440
aagttgacag tccttgcggc cgc                                            1463

<210> SEQ ID NO 22
<211> LENGTH: 15
<212> TYPE: DNA
<213> ORGANISM: Homo sapiens
<220> FEATURE:
<221> NAME/KEY: misc_feature
<223> OTHER INFORMATION: linker between VHA and VLB domains
<220> FEATURE:
<221> NAME/KEY: variation
<222> LOCATION: (15)..(15)
<223> OTHER INFORMATION: /replace="A may be substituted by T"

<400> SEQUENCE: 22
ggtggaggcg gttca                                                     15
```